US012582452B2

(12) United States Patent
Johnson et al.

(10) Patent No.: US 12,582,452 B2
(45) Date of Patent: Mar. 24, 2026

(54) DUAL COMPRESSION BONE IMPLANTS, SYSTEMS, AND METHODS

(71) Applicant: Vilex LLC, Park City, UT (US)

(72) Inventors: Brock Johnson, McMinnville, TN (US); Daniel J. Triplett, Smithfield, UT (US); Kyle Atwood, Richmond, UT (US)

(73) Assignee: Vilex LLC, Park City, UT (US)

( * ) Notice: Subject to any disclaimer, the term of this patent is extended or adjusted under 35 U.S.C. 154(b) by 276 days.

(21) Appl. No.: 18/368,526

(22) Filed: Sep. 14, 2023

(65) Prior Publication Data

US 2025/0090205 A1     Mar. 20, 2025

(51) Int. Cl.
   *A61B 17/72*          (2006.01)
(52) U.S. Cl.
   CPC ................................ *A61B 17/7291* (2013.01)
(58) Field of Classification Search
   CPC ............ A61B 17/7291; A61B 17/7216; A61B 17/7225
   See application file for complete search history.

(56) References Cited

U.S. PATENT DOCUMENTS

| | | |
|---|---|---|
| 9,241,744 B2 | 1/2016 | Blake et al. |
| 11,000,319 B2 | 5/2021 | Garlock et al. |
| 11,801,076 B2 | 10/2023 | Vicenzi et al. |
| 2005/0101958 A1* | 5/2005 | Adam .................... A61B 17/72 |
| | | 606/62 |

| | | | |
|---|---|---|---|
| 2008/0221577 A1* | 9/2008 | Elghazaly .......... | A61B 17/7241 |
| | | | 606/62 |
| 2010/0249781 A1* | 9/2010 | Haidukewych .... | A61B 17/7241 |
| | | | 606/62 |
| 2011/0004212 A1* | 1/2011 | Gall .................... | A61B 17/7225 |
| | | | 606/62 |
| 2011/0160729 A1* | 6/2011 | Overes ............... | A61B 17/7241 |
| | | | 606/286 |
| 2012/0130370 A1* | 5/2012 | Kinmon ............. | A61B 17/7241 |
| | | | 606/62 |
| 2012/0215222 A1* | 8/2012 | Yapp .................. | A61B 17/7291 |
| | | | 606/57 |
| 2024/0016522 A1 | 1/2024 | Stamp et al. | |

FOREIGN PATENT DOCUMENTS

WO      WO-2013134387 A1 *  9/2013  ........... A61B 17/725

* cited by examiner

*Primary Examiner* — Eduardo C Robert
*Assistant Examiner* — Anna V. Little
(74) *Attorney, Agent, or Firm* — David Meibos; Maywood IP Law

(57)          ABSTRACT

A system for providing dual compression to a bone joint may include an elongate device having a distal portion receivable within a distal bone tunnel formed in a distal bone of the bone joint, an intermediate portion receivable within an intermediate bone tunnel formed in an intermediate bone of the bone joint, and a proximal portion receivable within a proximal bone tunnel formed in a proximal bone of the bone joint. An intermediate carriage within the intermediate portion may couple with the intermediate bone and translate distally to provide a first compression force between the intermediate bone and the distal bone, and a proximal carriage within the proximal portion may couple with the proximal bone and translate distally to provide a second compression force between the proximal bone and the intermediate bone.

20 Claims, 20 Drawing Sheets

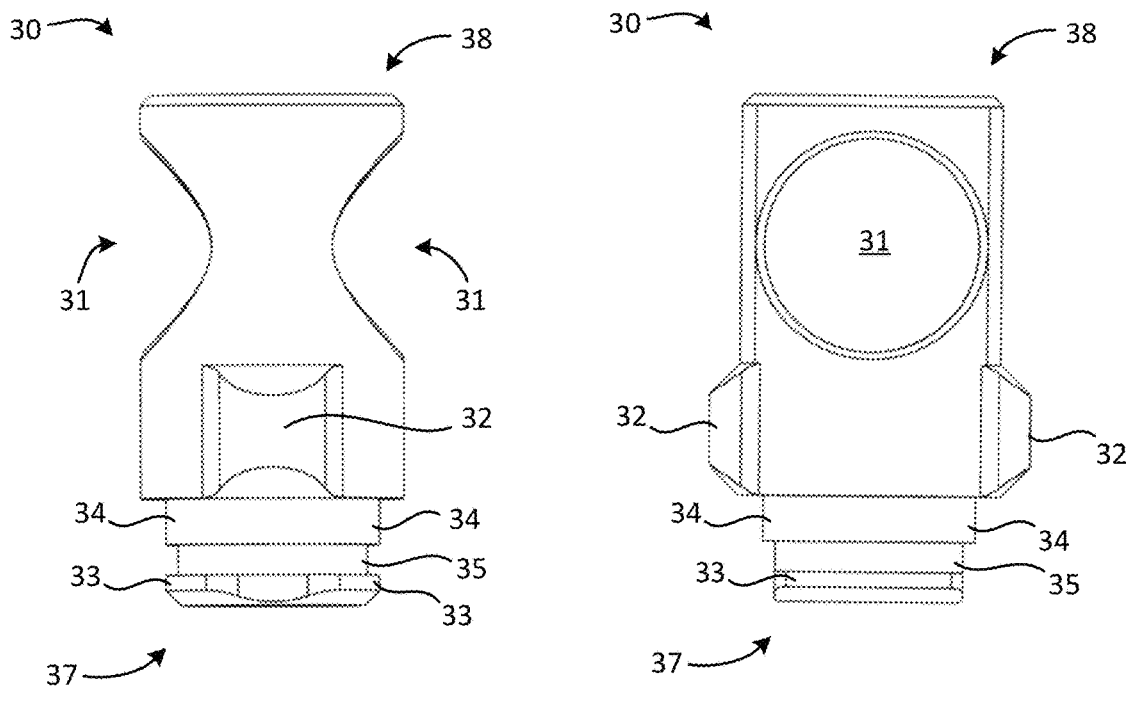
FIG. 5A          FIG. 5B
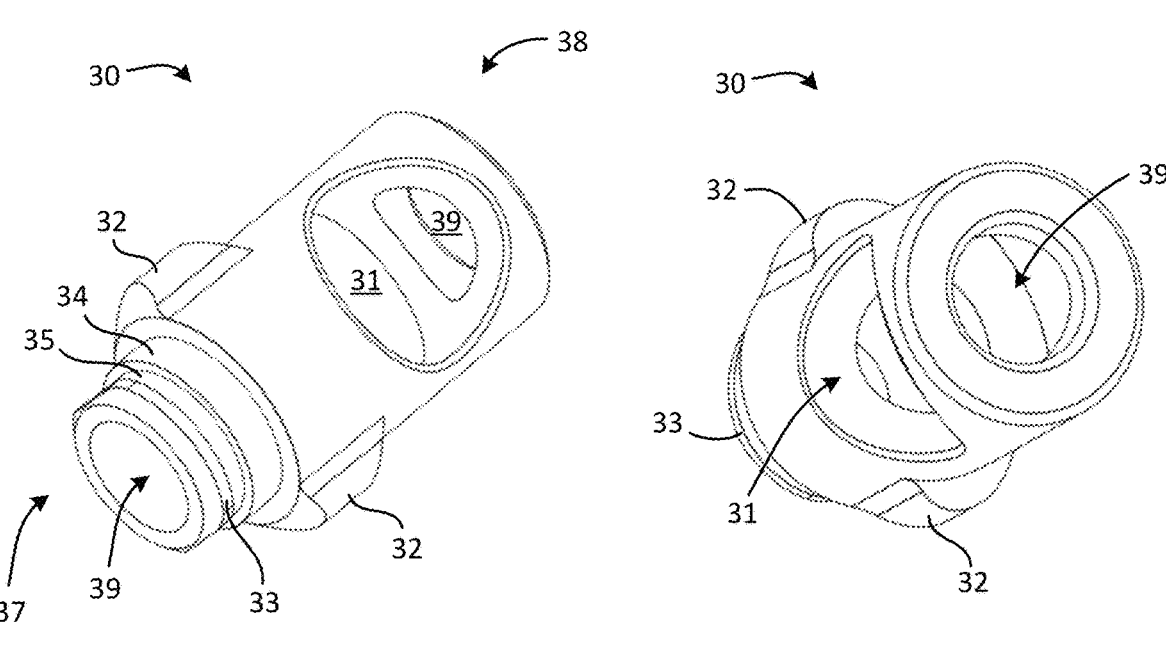
FIG. 5C          FIG. 5D

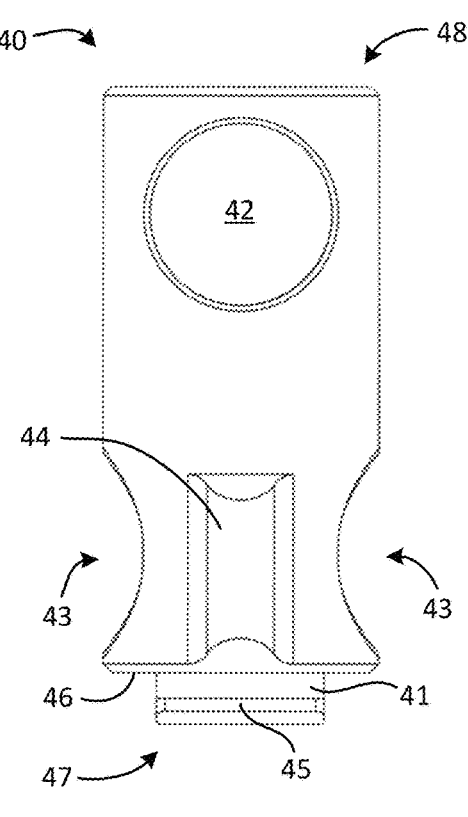
FIG. 6A
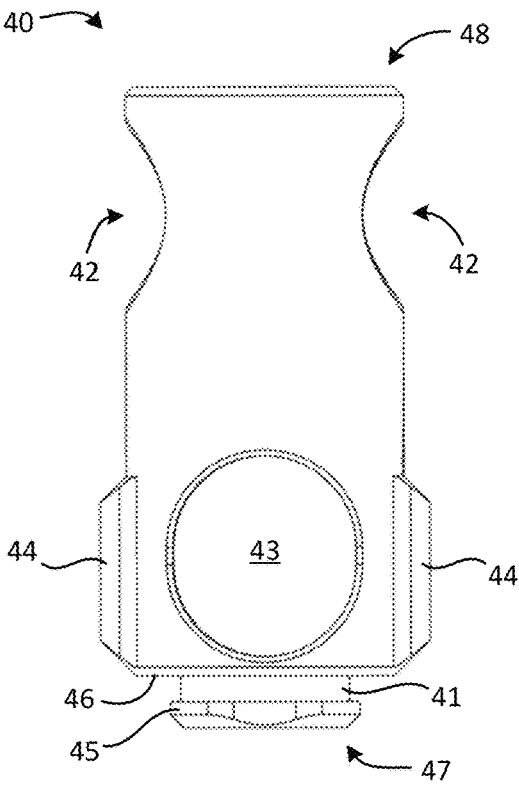
FIG. 6B
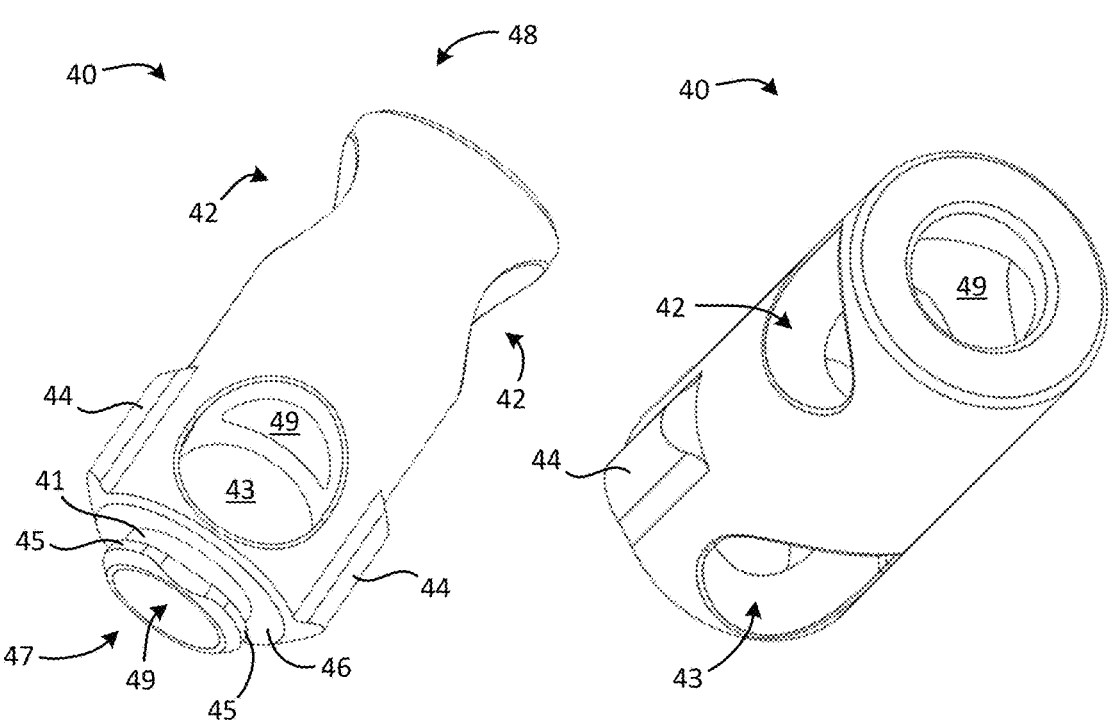
FIG. 6C                    FIG. 6D

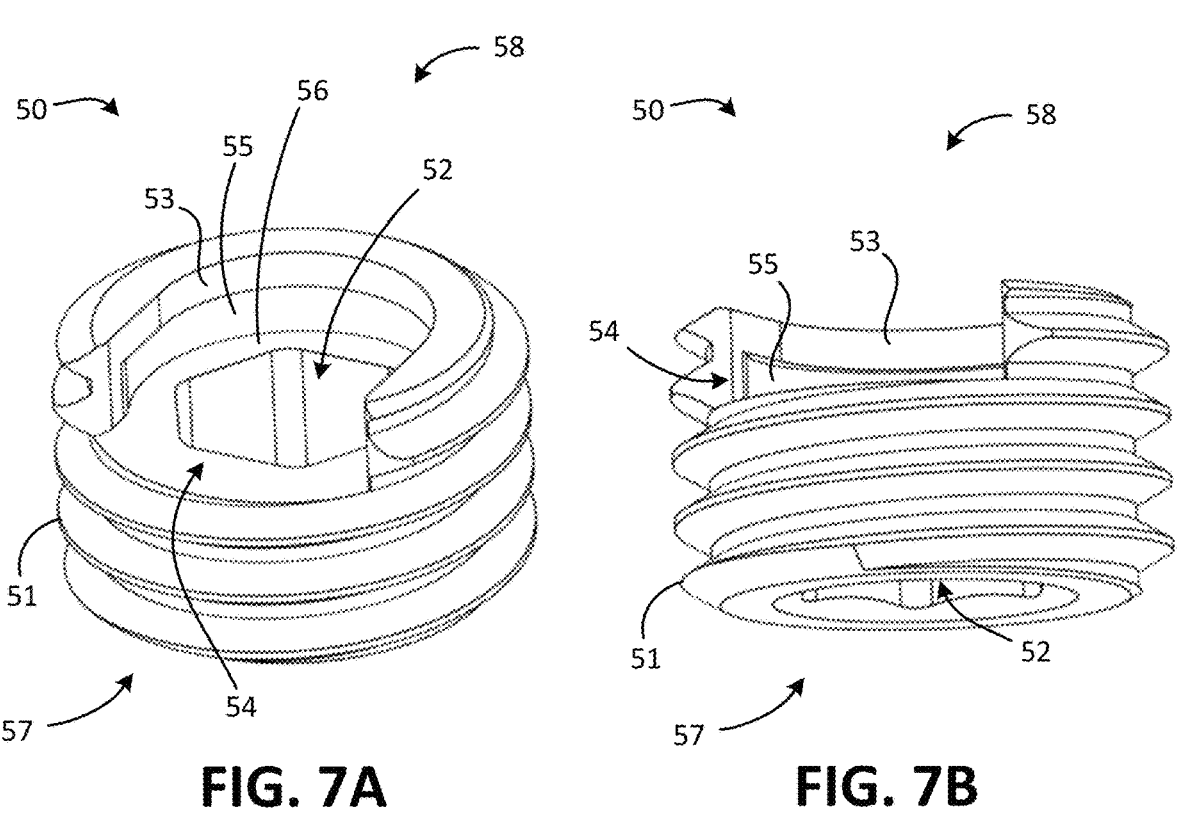
FIG. 7A          FIG. 7B
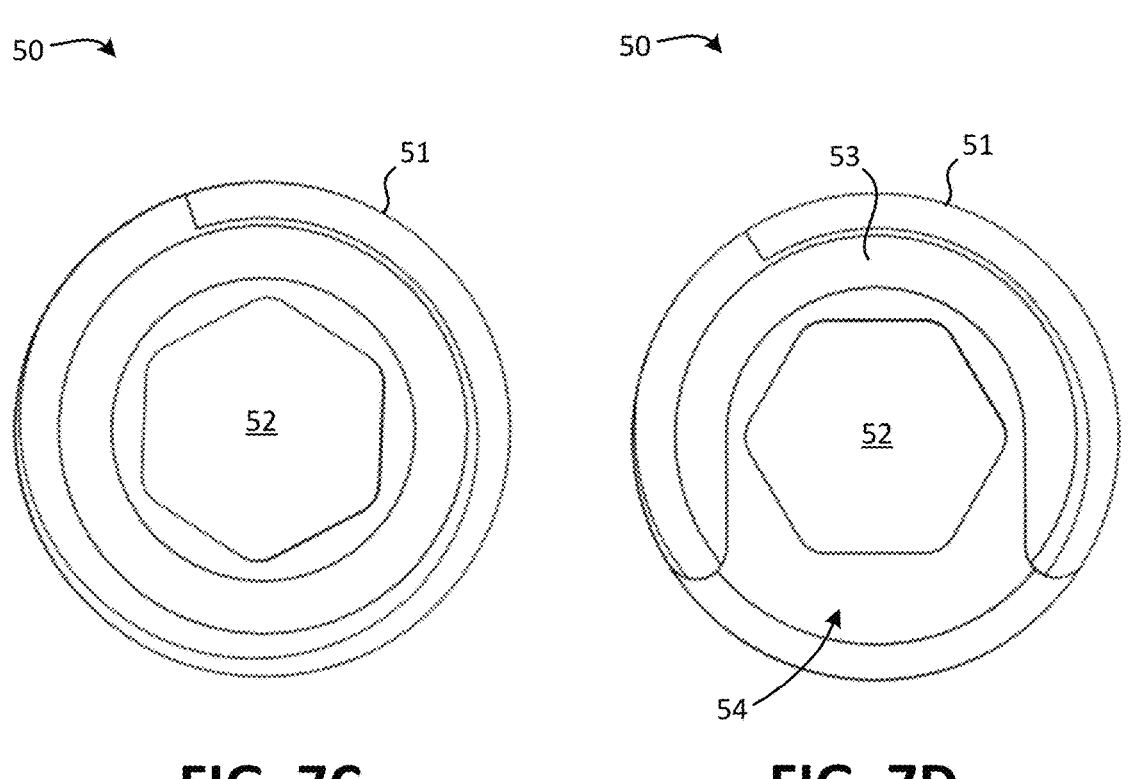
FIG. 7C          FIG. 7D

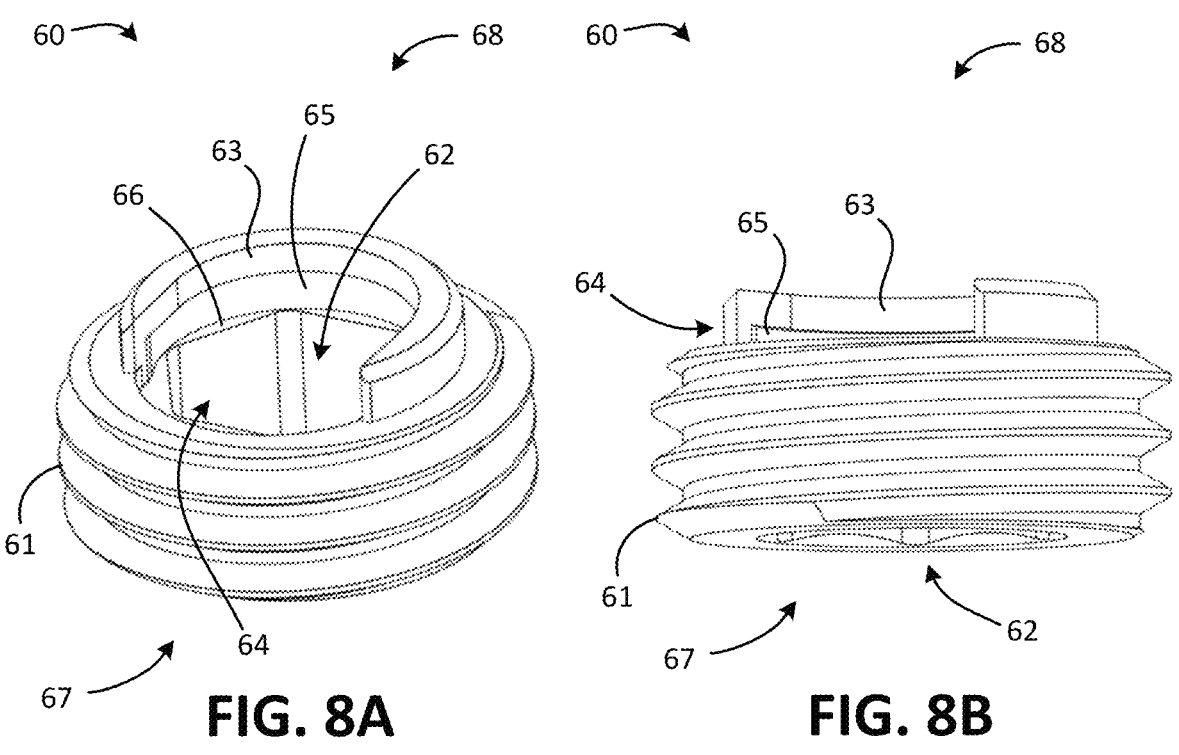
FIG. 8A
FIG. 8B
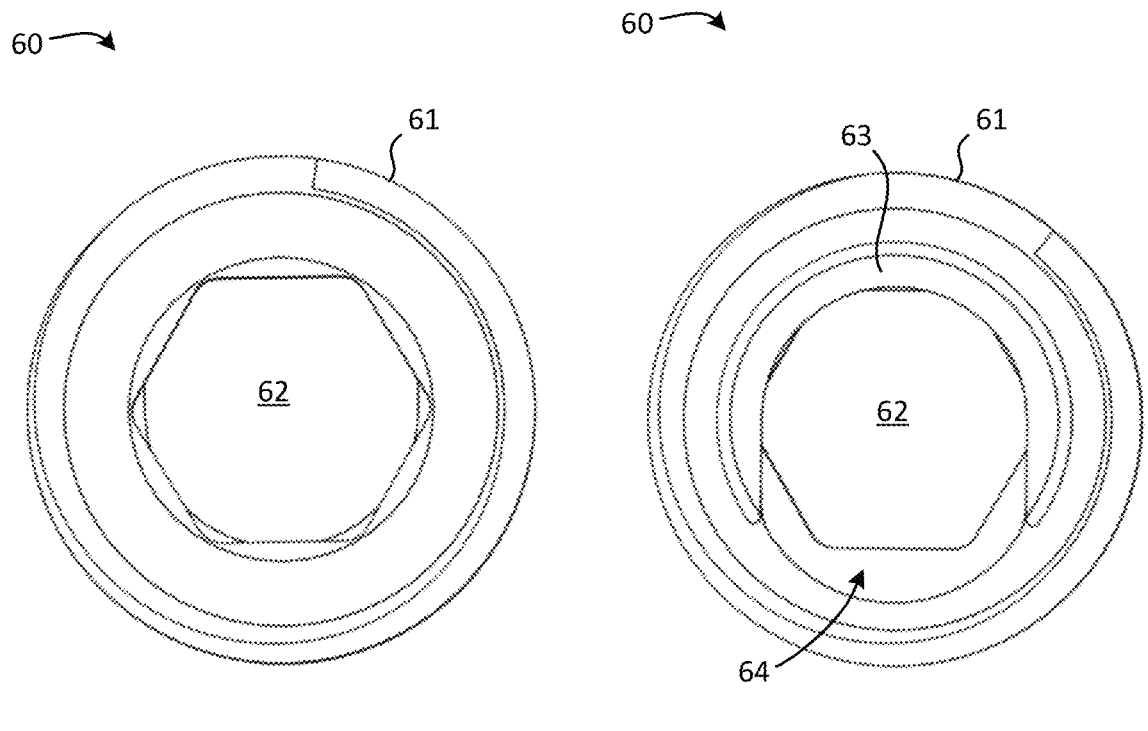
FIG. 8C
FIG. 8D

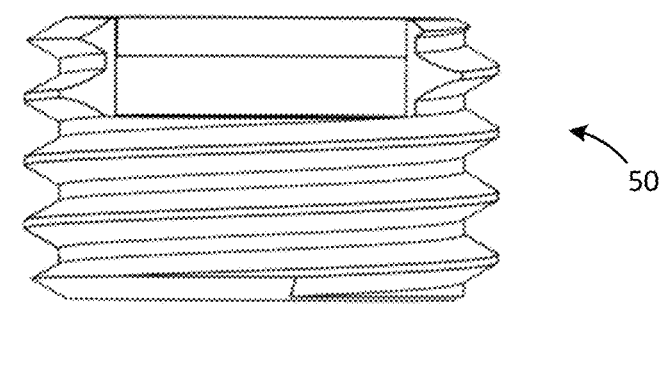
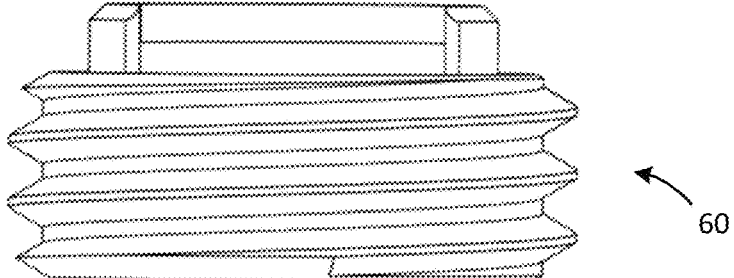
FIG. 9
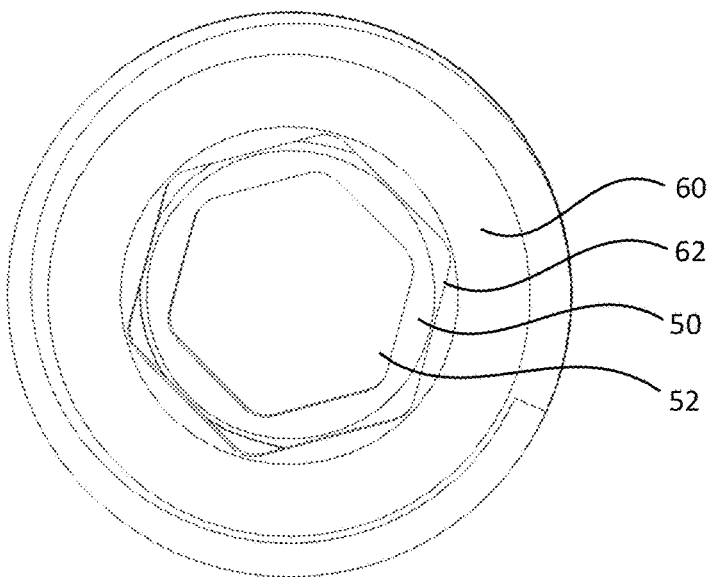
FIG. 10

DUAL COMPRESSION BONE IMPLANTS, SYSTEMS, AND METHODS

TECHNICAL FIELD

The present disclosure relates to bone implants, systems, and methods. More specifically, the present disclosure relates to dual compression bone joint implants, systems, and methods with improved structures and techniques for providing dual compression to bone joints.

BACKGROUND

Bone joint fusion procedures may be utilized in certain circumstances to help improve quality of life for patients suffering from one or more of the following example conditions: post-traumatic or degenerative arthritis/arthrosis, a previously infected arthrosis, revision of a failed joint arthrodesis/fusion (e.g., a failed tibio-talo-calcaneal arthrodesis), a failed total joint arthroplasty, avascular necrosis of a bone joint, neuromuscular deformity or other neuromuscular diseases with severe deformity or instability of a bone joint, rheumatoid arthritis, osteoarthritis, a nonunion or pseudarthrosis of a bone joint, trauma (e.g., a severe or malunited tibial pilon fracture, etc.), Charcot foot, severe end stage degenerative arthritis, instability and/or skeletal defects after tumor resection, neuroarthropathy or neuropathic bone joint deformity, severe bone joint deformities, an absent bone from a bone joint, etc.

However, providing adequate stability, strength, and compression maintenance for bone joints comprising a distal bone, an intermediate bone, and a proximal bone can be difficult to achieve during the fusion healing process.

Accordingly, bone joint implants, systems, and methods with improved structures that can provide dual compression techniques to achieve additional stability, strength, and compression maintenance during the fusion healing process would be desirable.

SUMMARY

The various implants, systems, and methods of the present disclosure have been developed in response to the present state of the art, and in particular, in response to the problems and needs in the art that have not yet been fully solved by currently available joint implants, systems, and methods. In some embodiments, the joint implants, systems, and methods of the present disclosure may provide improved fixation and stability for bone joints during the fusion process.

In some embodiments, a system for providing dual compression to an ankle joint may include an intramedullary nail, a talar compression carriage, and a calcaneal compression carriage. The intramedullary nail may include a distal portion configured to be at least partially received within an intramedullary canal of a tibial bone of the ankle joint, an intermediate portion receivable within a first bone tunnel formed through a talar bone of the ankle joint, and a proximal portion receivable within a second bone tunnel formed through a calcaneal bone of the ankle joint. The talar compression carriage may be receivable within the intermediate portion of the intramedullary nail, and the calcaneal compression carriage may be receivable within the proximal portion of the intramedullary nail. The talar compression carriage may be configured to couple with the talar bone and translate distally within the intermediate portion of the intramedullary nail to provide a first compression force between the talar bone and the tibial bone of the ankle joint.

The calcaneal compression carriage may be configured to couple with the calcaneal bone and translate distally within the proximal portion of the intramedullary nail to provide a second compression force between the calcaneal bone and the talar bone of the ankle joint.

In some embodiments, the system may also include a first bone fixation device configured to couple the talar bone to the talar compression carriage, and a second bone fixation device configured to couple the calcaneal bone to the calcaneal compression carriage.

In some embodiments of the system, the intermediate portion of the intramedullary nail may include a first elongated window formed through the intermediate portion and configured to receive the first bone fixation device therethrough, and the proximal portion of the intramedullary nail may include a second elongated window formed through the proximal portion and configured to receive the second bone fixation device therethrough.

In some embodiments of the system, the talar compression carriage may include a first hole configured to receive the first bone fixation device therein to couple the talar bone to the talar compression carriage, and the calcaneal compression carriage may include a second hole configured to receive the second bone fixation device therein to couple the calcaneal bone to the calcaneal compression carriage.

In some embodiments of the system, the intermediate portion of the intramedullary nail may include an intermediate chamber configured to translatably receive the talar compression carriage therein, and the proximal portion of the intramedullary nail may include a proximal chamber configured to translatably receive the calcaneal compression carriage therein.

In some embodiments of the system, the talar compression carriage may include a first anti-rotation tab configured to be received within a first anti-rotation slot formed in the intermediate chamber to prevent the talar compression carriage from rotating as the talar compression carriage translates within the intermediate chamber. The calcaneal compression carriage may also include a second anti-rotation tab configured to be received within a second anti-rotation slot formed in the proximal chamber to prevent the calcaneal compression carriage from rotating as the calcaneal compression carriage translates within the proximal chamber.

In some embodiments of the system, the intermediate chamber may include a first internal thread configured to threadingly engage a first set screw configured to urge the talar compression carriage distally to provide the first compression force between the talar bone and the tibial bone of the ankle joint. The proximal chamber may also include a second internal thread configured to threadingly engage a second set screw configured to urge the calcaneal compression carriage distally to provide the second compression force between the calcaneal bone and the talar bone of the ankle joint.

In some embodiments, a system for providing dual compression to a bone joint may include an elongate device, an intermediate carriage, and a proximal carriage. The elongate device may include a distal portion receivable within a distal bone tunnel formed in a distal bone of the bone joint, an intermediate portion receivable within an intermediate bone tunnel formed in an intermediate bone of the bone joint, and a proximal portion receivable within a proximal bone tunnel formed in a proximal bone of the bone joint. The intermediate carriage may be receivable within the intermediate portion of the elongate device, and the proximal carriage may be receivable within the proximal portion of the elongate device. The intermediate carriage may be configured to couple with the intermediate bone and translate distally within the intermediate portion of the elongate device to provide a first compression force between the intermediate bone and the distal bone of the bone joint. The proximal carriage may be configured to couple with the proximal bone and translate distally within the proximal portion of the elongate device to provide a second compression force between the proximal bone and the intermediate bone of the bone joint.

In some embodiments, the system may also include a first bone fixation device configured to couple the intermediate bone to the intermediate carriage, and a second bone fixation device configured to couple the proximal bone to the proximal carriage.

In some embodiments of the system, the intermediate portion of the elongate device may include a first window configured to receive the first bone fixation device therethrough, and the proximal portion of the elongate device may include a second window configured to receive the second bone fixation device therethrough.

In some embodiments of the system, the intermediate carriage may include a first passageway configured to receive the first bone fixation device therethrough to couple the intermediate bone to the intermediate carriage, and the proximal carriage may include a second passageway configured to receive the second bone fixation device therethrough to couple the proximal bone to the proximal carriage.

In some embodiments of the system, the intermediate portion of the elongate device may include an intermediate chamber configured to translatably receive the intermediate carriage therein, and the proximal portion of the elongate device may include a proximal chamber configured to translatably receive the proximal carriage therein.

In some embodiments of the system, the intermediate carriage may include a first anti-rotation tab receivable within a first anti-rotation slot formed in the intermediate chamber to prevent the intermediate carriage from rotating as the intermediate carriage translates within the intermediate chamber, and the proximal carriage may include a second anti-rotation tab receivable within a second anti-rotation slot formed in the proximal chamber to prevent the proximal carriage from rotating as the proximal carriage translates within the proximal chamber.

In some embodiments of the system, the intermediate chamber may include a first internal thread configured to threadingly engage a first set screw that urges the intermediate carriage distally to provide the first compression force between the intermediate bone and the distal bone of the bone joint, and the proximal chamber may include a second internal thread configured to threadingly engage a second set screw that urges the proximal carriage distally to provide the second compression force between the proximal bone and the intermediate bone of the bone joint.

In some embodiments, a method for providing dual compression to a bone joint may include inserting a distal portion of an elongate device through a proximal bone tunnel formed in a proximal bone of the bone joint, through an intermediate bone tunnel formed in an intermediate bone of the bone joint, and into a distal bone tunnel formed in a distal bone of the bone joint. The method may also include coupling the intermediate bone to an intermediate carriage housed within an intermediate portion of the elongate device and translating the intermediate carriage distally within the intermediate portion of the elongate device to provide a first compression force between the intermediate bone and the distal bone of the bone joint. The method may further include coupling the proximal bone to a proximal carriage housed within a proximal portion of the elongate device and translating the proximal carriage distally within the proximal portion of the elongate device to provide a second compression force between the proximal bone and the intermediate bone of the bone joint.

In some embodiments of the method, coupling the intermediate bone to the intermediate carriage may also include inserting a first bone fixation device through the intermediate bone, through a first window formed in the intermediate portion, and into a first passageway formed in the intermediate carriage to couple the intermediate bone to the intermediate carriage.

In some embodiments of the method, translating the intermediate carriage distally within the intermediate portion may also include rotating a first set screw to urge the intermediate carriage distally and provide the first compression force between the intermediate bone and the distal bone of the bone joint.

In some embodiments of the method, coupling the proximal bone to the proximal carriage may also include inserting a second bone fixation device through the proximal bone, through a second window formed in the proximal portion, and into a second passageway formed in the proximal carriage to couple the proximal bone to the proximal carriage.

In some embodiments of the method, translating the proximal carriage distally within the proximal portion may also include rotating a second set screw to urge the proximal carriage distally and provide the second compression force between the proximal bone and the intermediate bone of the bone joint.

In some embodiments, the method may also include inserting a third bone fixation device through the proximal bone, through a third window formed in the proximal portion, and into a third passageway formed in the proximal carriage to couple the proximal bone to the proximal carriage.

These and other features and advantages of the present disclosure will become more fully apparent from the following description and appended claims or may be learned by the practice of the implants, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 5A illustrates a right side view of an intermediate carriage of the implant system shown in FIG. 1, according to an embodiment of the present disclosure;

FIG. 5B illustrates a front side view of the intermediate carriage of FIG. 5A;

FIG. 5C illustrates a bottom perspective view of the intermediate carriage of FIG. 5A;

FIG. 5D illustrates a top perspective view of the intermediate carriage of FIG. 5A;

FIG. 6A illustrates a front side view of a proximal carriage of the implant system shown in FIG. 1, according to an embodiment of the present disclosure;

FIG. 6B illustrates a right side view of the proximal carriage of FIG. 6A;

FIG. 6C illustrates a bottom perspective view of the proximal carriage of FIG. 6A;

FIG. 6D illustrates a top perspective view of the proximal carriage of FIG. 6A;

FIG. 7A illustrates a top perspective view of an intermediate set screw of the implant system shown in FIG. 1, according to an embodiment of the present disclosure;

FIG. 7B illustrates a bottom perspective view of the intermediate set screw of FIG. 7A;

FIG. 7C illustrates a bottom view of the intermediate set screw of FIG. 7A;

FIG. 7D illustrates a top view of the intermediate set screw of FIG. 7A;

FIG. 8A illustrates a top perspective view of a proximal set screw of the implant system shown in FIG. 1, according to an embodiment of the present disclosure;

FIG. 8B illustrates a bottom perspective view of the proximal set screw of FIG. 8A;

FIG. 8C illustrates a bottom view of the proximal set screw of FIG. 8A;

FIG. 8D illustrates a top view of the proximal set screw of FIG. 8A;

FIG. 9 illustrates a side view of the intermediate set screw of FIG. 7A relative to the proximal set screw of FIG. 8A;

FIG. 10 illustrates a bottom view of the intermediate set screw relative to the proximal set screw from FIG. 9;

Figure 1:
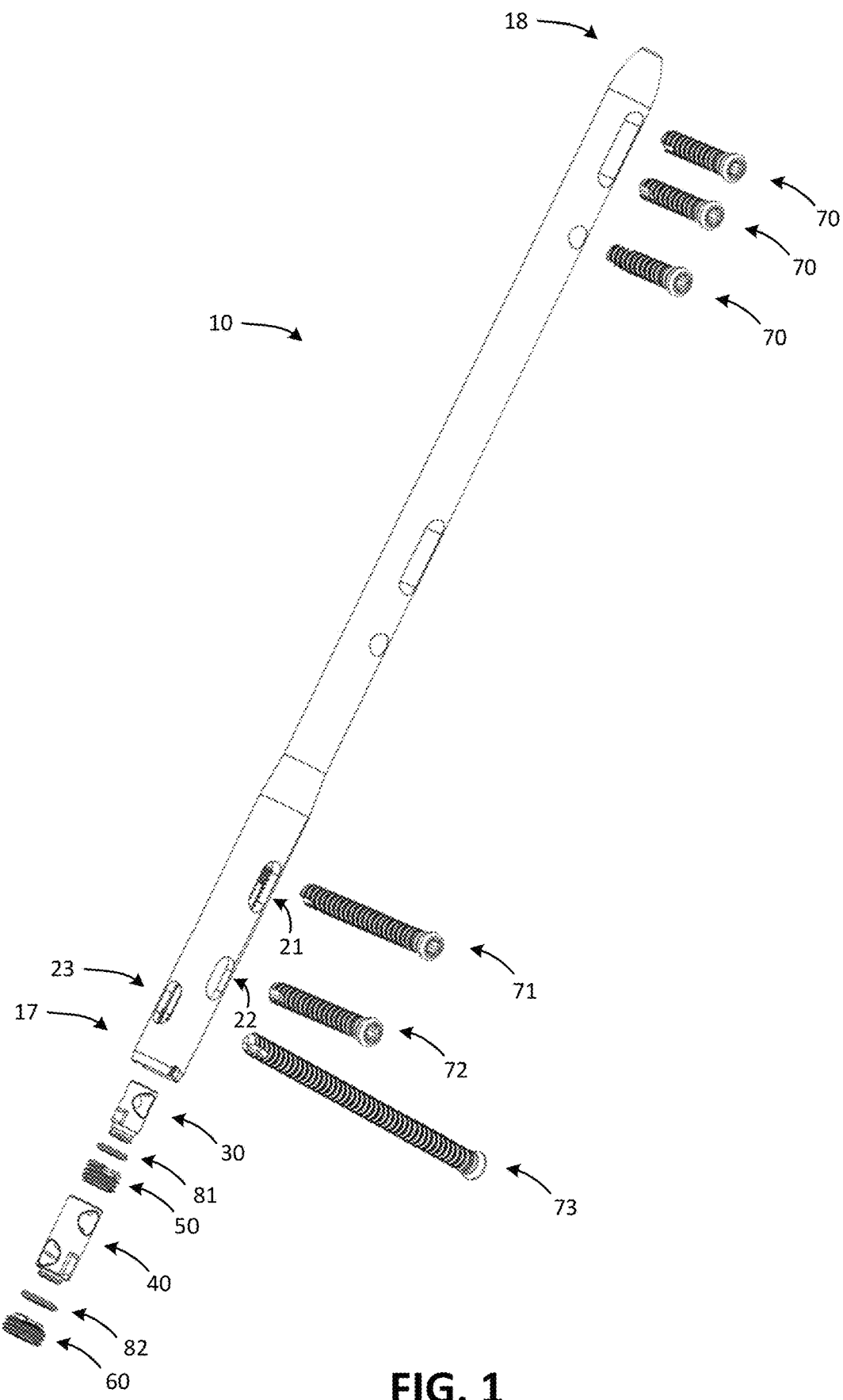
FIG. 1 illustrates an exploded view of an implant system for providing dual compression to a bone joint, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms may also be generally applicable to physical objects.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

Although the following detailed description utilizes the ankle joint as an example application for the concepts disclosed herein, it will also be understood that the general concepts, structures, systems, and techniques that are disclosed or contemplated herein may be adapted for use in any bone or bone joint of the body, including but not limited to: any bone or bone joint of the foot, any bone or bone joint of the hand, any bone or bone joint of the wrist, any bone or bone joint of the spine, etc.

Figure 2:
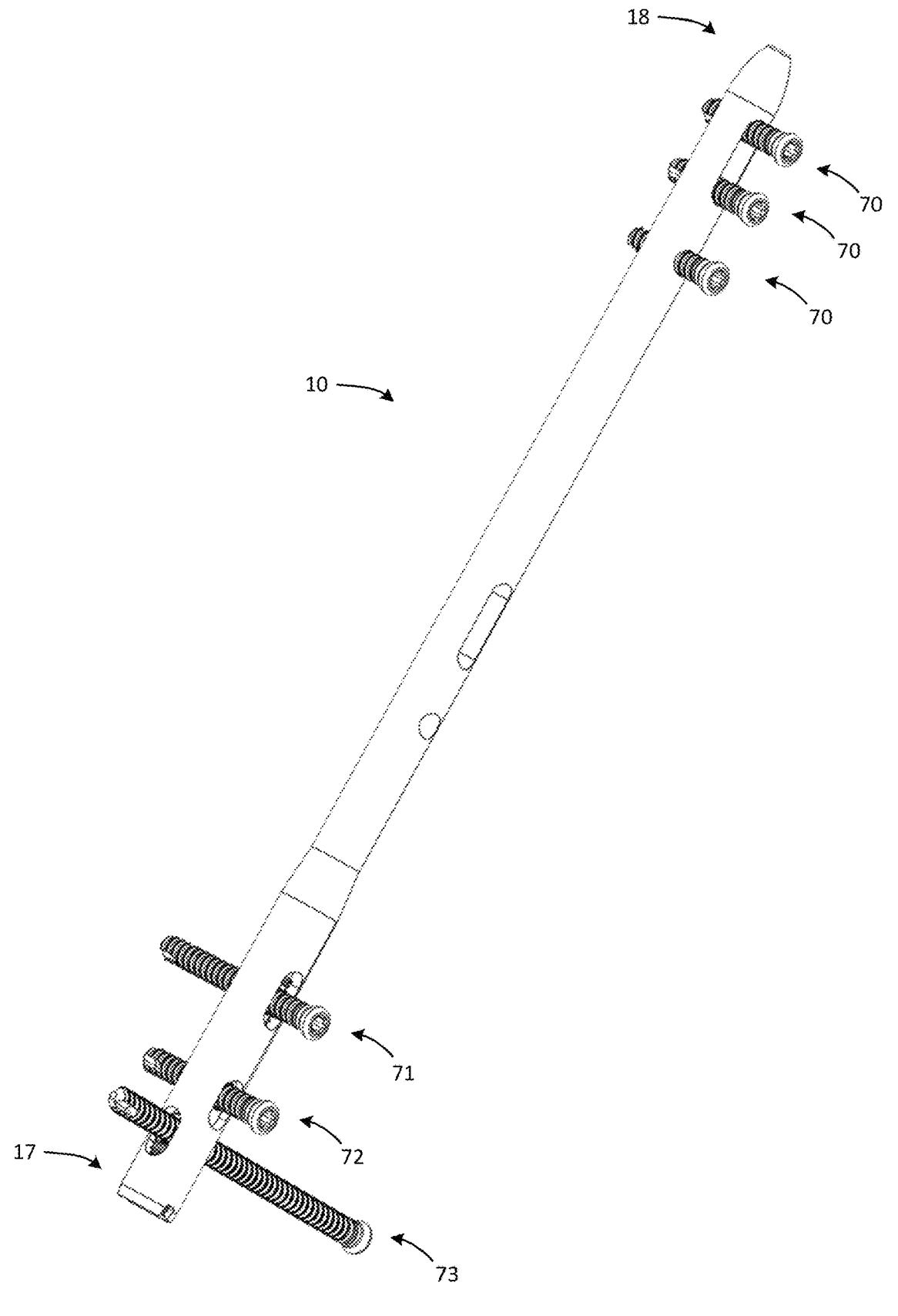
FIG. 2 illustrates a perspective view of the implant system of FIG. 1, after assembly.
Figure 3:
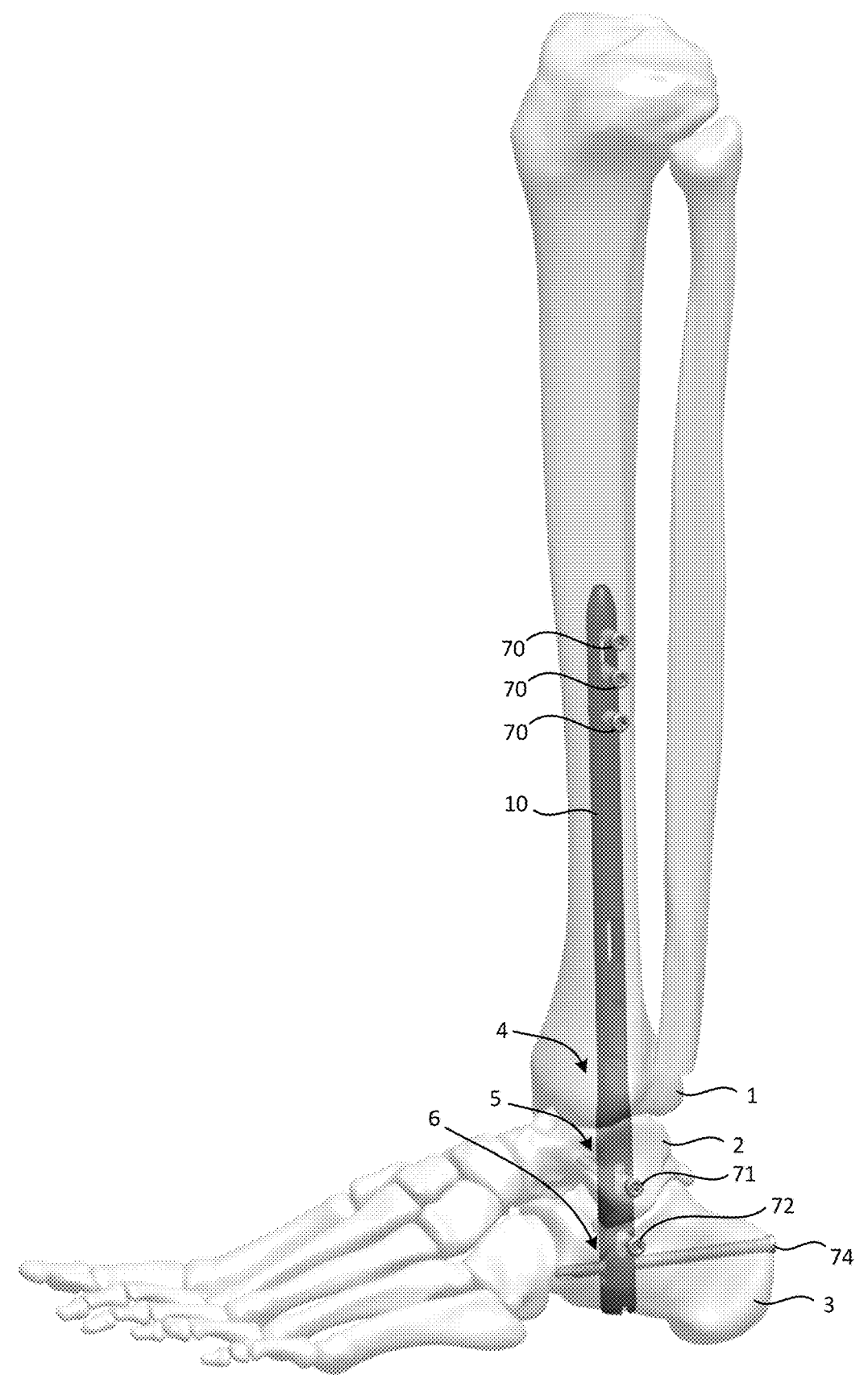
FIG. 3 illustrates a perspective view of the implant system of FIG. 1 installed in an ankle joint.
Figure 11:
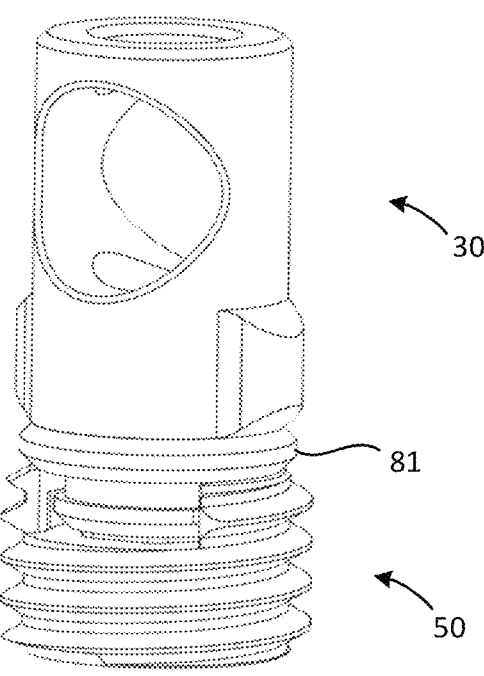
FIG. 11 illustrates a perspective side view of an intermediate carriage, an intermediate carriage spacer, and an intermediate set screw assembled together.
Figure 12:
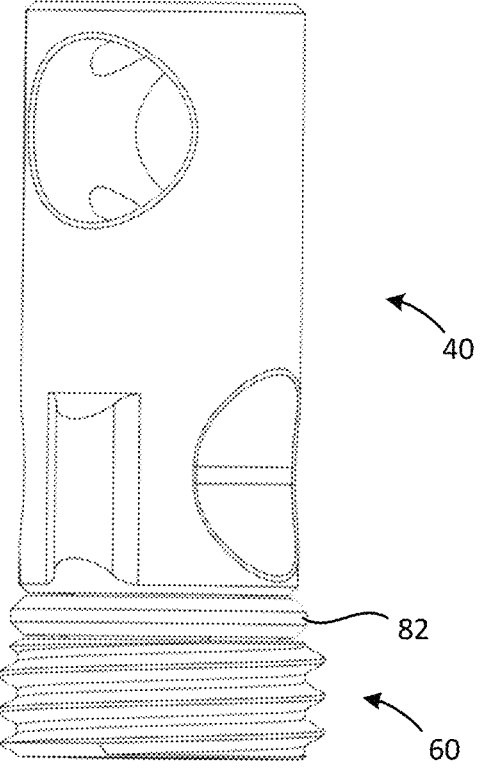
FIG. 12 illustrates a perspective side view of a proximal carriage, a proximal carriage spacer, and a proximal set screw assembled together.

FIGS. 1-12 illustrate various views of an example implant system and its components for providing dual compression to a bone joint (such as an ankle bone joint), according to an embodiment of the present disclosure. Specifically: FIG. 1 shows an exploded view of the implant system; FIG. 2 shows the implant system assembled together; FIG. 3 shows the implant system installed in an ankle joint; FIGS. 4A-4E show various views of an intramedullary nail or elongate device 10 of the implant system; FIGS. 5A-5D show various views of a talar compression carriage or intermediate carriage 30 of the implant system; FIGS. 6A-6D show various views of a calcaneal compression carriage or proximal carriage 40 of the implant system; FIGS. 7A-7D show various views of an intermediate bone compression member, first set screw, or intermediate set screw 50 of the implant system; FIGS. 8A-8D show various views of a proximal bone compression member, second set screw, or proximal set screw 60 of the implant system; FIGS. 9-10 show the intermediate set screw 50 and the proximal set screw 60 relative to each other; and FIGS. 11-12 show intermediate carriage and proximal carriage assemblies prior to insertion within the elongate device 10.

FIGS. 1-3 show how, in at least some embodiments, the implant system may generally comprise: the elongate device 10, the intermediate carriage 30, the proximal carriage 40, the intermediate set screw 50, the proximal set screw 60, an intermediate carriage spacer 81, a proximal carriage spacer 82, an intermediate or first bone fixation device 71, an upper proximal or second bone fixation device 72, a lower proximal or third bone fixation device 73, and one or more distal bone fixation devices 70.

FIGS. 4A-4E show various views of the elongate device 10 from the implant system shown in FIGS. 1-3, according to an embodiment of the present disclosure. The elongate device 10 may generally include: a proximal end 17, a distal end 18, a distal portion 11, a transition zone or tapered portion 29, an intermediate portion 12, and a proximal portion 13.

In some embodiments, the elongate device 10 may generally comprise one or more cylindrical and/or cone shapes aggregated together. However, it will be understood that other embodiments of the elongate device 10 may comprise any shape or aggregation of shapes suitable for use in one or more bones of a bone joint (not shown).

In some embodiments, the distal end 18 of the elongate device 10 may be rounded, narrowed, or pointed to facilitate insertion of the elongate device 10 into bone.

In some embodiments, the distal portion 11 of the elongate device 10 may include one or more distal holes 19 formed through the elongate device 10 and configured to receive one or more distal bone fixation devices 70 therethrough to affix the distal portion 11 of the elongate device 10 to a distal bone, such as a tibial bone 1 as one non-limiting example.

In some embodiments, the one or more distal holes 19 may comprise one or more circular or static holes configured to receive a distal bone fixation device therethrough to statically secure the distal portion 11 of the elongate device 10 to the distal bone.

In some embodiments, the one or more distal holes 19 may comprise one or more elongated, oval, or dynamic holes configured to receive at least one distal bone fixation device therethrough to dynamically secure the distal portion 11 of the elongate device 10 to the distal bone.

Figure 4A:
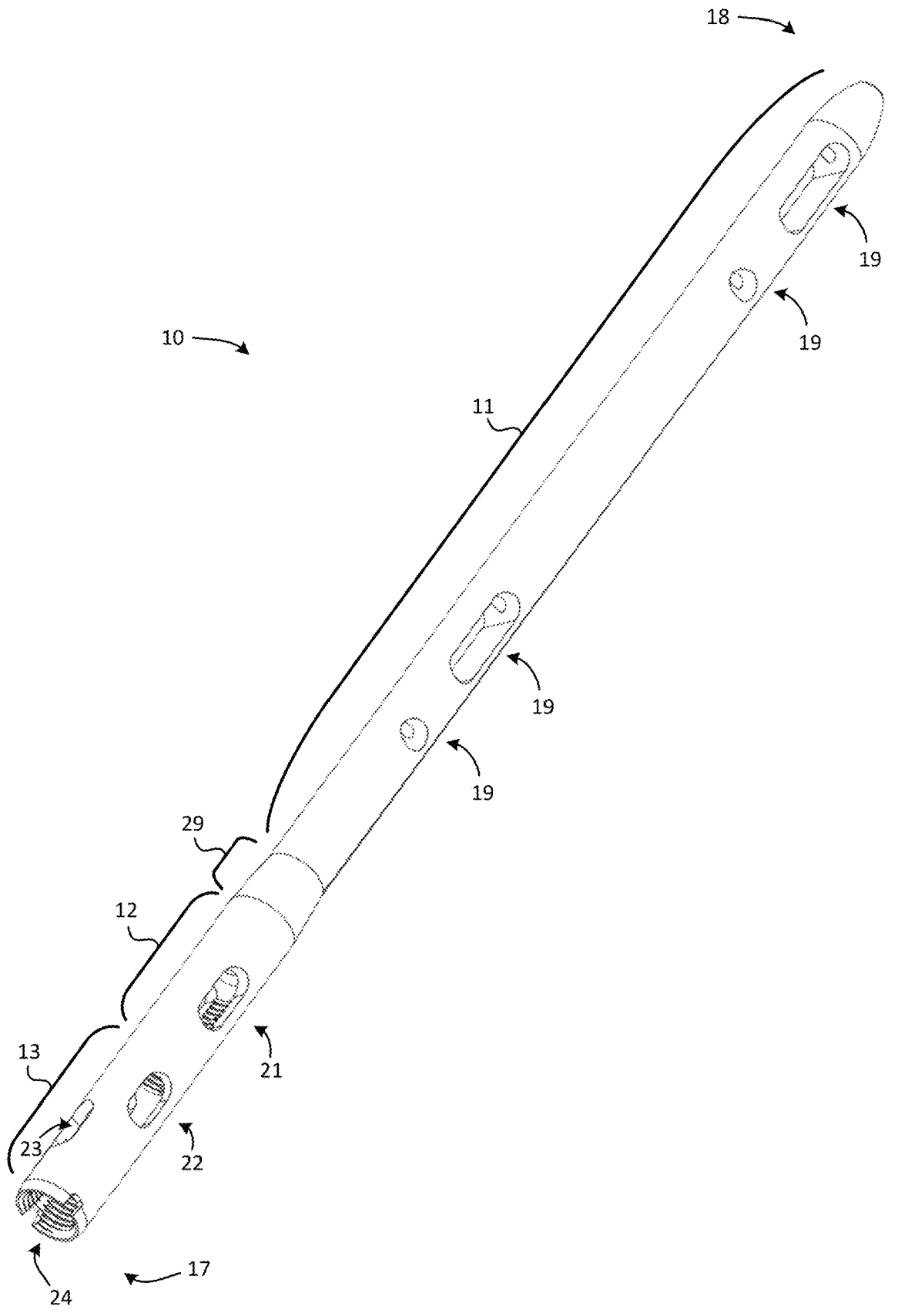
FIG. 4A illustrates a bottom perspective view of an elongate device of the implant system shown in FIG. 1, according to an embodiment of the present disclosure.
Figure 4B:
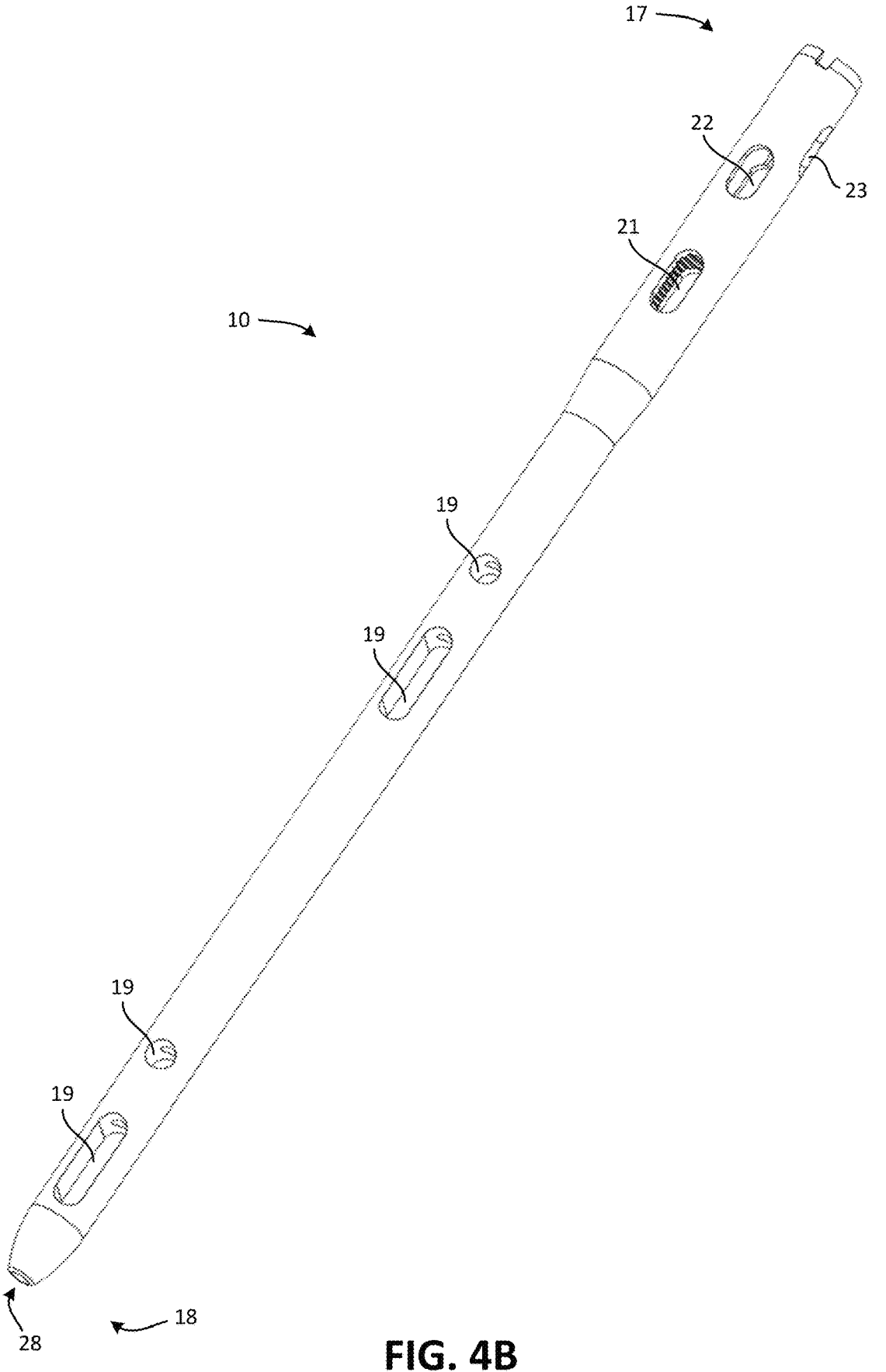
FIG. 4B illustrates a top perspective view of the elongate device of FIG. 4A.
Figures 4C, 4D, 4E:
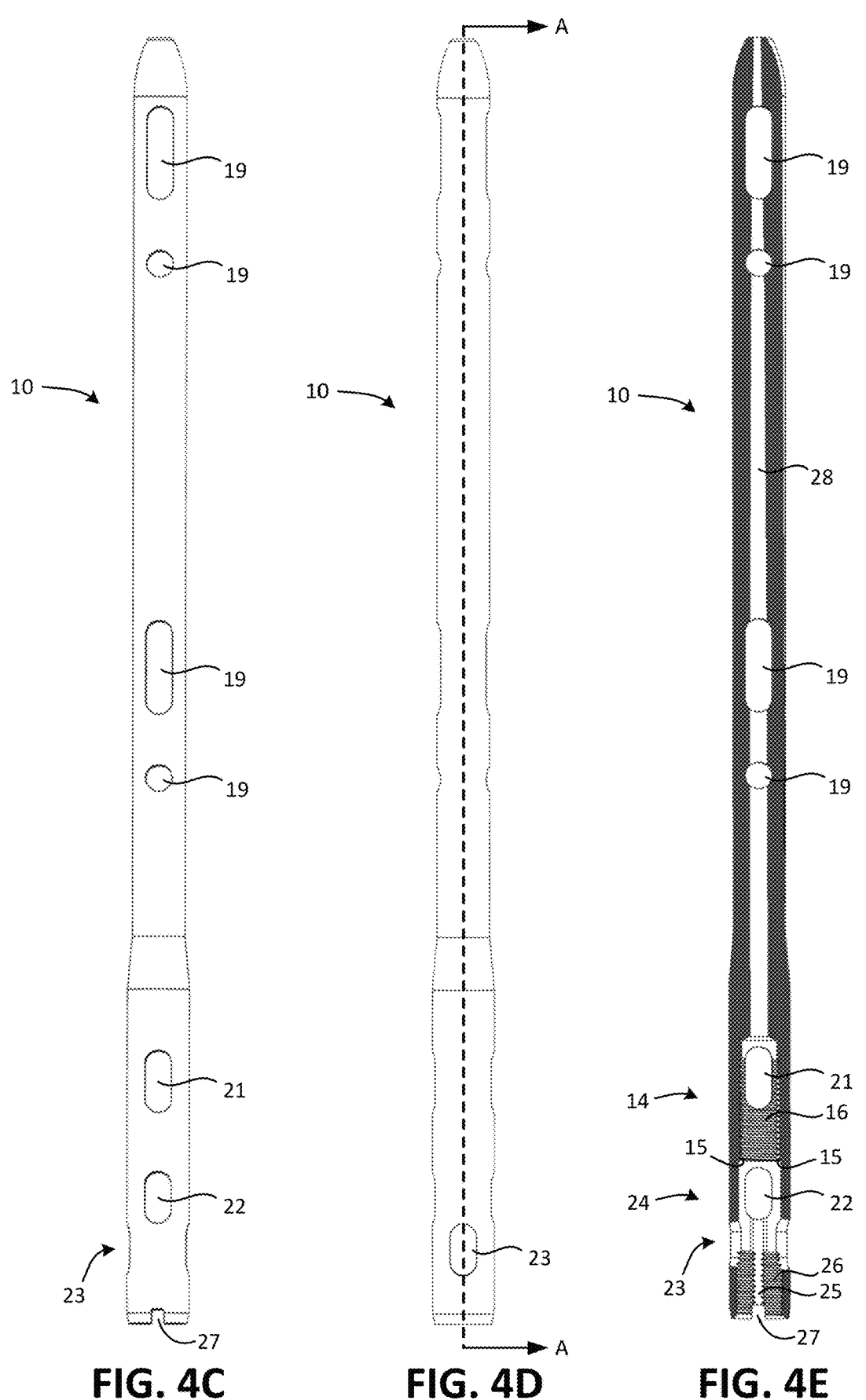
FIG. 4C illustrates a front side view of the elongate device of FIG. 4A.
FIG. 4D illustrates a right side view of the elongate device of FIG. 4A.
FIG. 4E illustrates a cross-sectional side view of the elongate device of FIG. 4A, taken along the line A-A in FIG. 4D.

In some embodiments, the elongate device 10 may be cannulated and may include an elongate device longitudinal passageway 28, as shown in FIG. 4E. In these embodiments, the elongate device longitudinal passageway 28 may receive a guide wire therethrough, as will be discussed below in more detail.

In some embodiments, the intermediate portion 12 of the elongate device 10 may include an intermediate portion window 21 formed therethrough, as well as an intermediate portion chamber 14 formed within the intermediate portion 12 of the elongate device 10.

In some embodiments, the intermediate portion chamber 14 may include a first internal thread or intermediate chamber thread 16 formed therein.

In some embodiments, the intermediate portion chamber 14 may include one or more first anti-rotation slots or an intermediate chamber anti-rotation slot 15 formed therein, as will be discussed below in more detail.

In some embodiments, proximal portion 13 of the elongate device 10 may include an upper proximal portion window 22 and/or a lower proximal portion window 23 formed therethrough, as well as a proximal portion chamber 24 formed within the proximal portion 13 of the elongate device 10.

In some embodiments, the proximal portion chamber 24 may include a second internal thread or proximal chamber thread 26 formed therein.

In some embodiments, the proximal portion chamber 24 may include one or more second anti-rotation slots or a proximal chamber anti-rotation slot 25 formed therein, as will be discussed below in more detail.

In some embodiments, the proximal end 17 of the elongate device 10 may include one or more notches 27 formed therein, as will be discussed below in more detail.

FIGS. 5A-5D show various views of the intermediate carriage 30 from the implant system shown in FIG. 1, according to an embodiment of the present disclosure. The intermediate carriage 30 may generally include: a proximal end 37, a distal end 38, an intermediate carriage longitudinal passageway 39, a first hole/passageway or intermediate carriage hole 31, one or more first anti-rotation tabs or an intermediate carriage anti-rotation tab 32, an intermediate carriage lower ledge 33, an intermediate carriage upper ledge 34, and an intermediate carriage neck 35.

In some embodiments, the intermediate carriage 30 may generally comprise a cylindrical shape. However, it will be understood that the intermediate carriage 30 may comprise any shape suitable for use within the intermediate portion chamber 14.

FIGS. 6A-6D show various views of the proximal carriage 40 from the implant system shown in FIG. 1, according to an embodiment of the present disclosure. The proximal carriage 40 may generally include: a proximal end 47, a distal end 48, a proximal carriage longitudinal passageway 49, a second hole/passageway or upper proximal carriage hole 42, a third hole/passageway or lower proximal carriage hole 43, one or more second anti-rotation tabs or a proximal carriage anti-rotation tab 44, a proximal carriage lower ledge 45, a proximal carriage upper ledge 46, a proximal carriage neck 41.

In some embodiments, the proximal carriage 40 may generally comprise a cylindrical shape. However, it will be understood that the proximal carriage 40 may comprise any shape suitable for use within the proximal portion chamber 24.

FIGS. 7A-7D show various views of the intermediate set screw 50 from the implant system shown in FIG. 1, according to an embodiment of the present disclosure. The intermediate set screw 50 may generally include: a proximal end 57, a distal end 58, an intermediate set screw thread 51, an intermediate set screw driver engagement feature 52, an intermediate set screw retaining ledge 53, an intermediate set screw loading slot 54, and an intermediate set screw recess 55.

In some embodiments, the intermediate set screw driver engagement feature 52 may comprise a hexagonal shape. However, it will be understood that any driver engagement feature style or shape may be utilized without departing from the spirit or scope of the present disclosure.

FIGS. 8A-8D show various views of the proximal set screw 60 from the implant system shown in FIG. 1, according to an embodiment of the present disclosure. The proximal set screw 60 may generally include: a proximal end 67, a distal end 68, a proximal set screw thread 61, a proximal set screw driver engagement feature 62, a proximal set screw retaining ledge 63, a proximal set screw loading slot 64, and a proximal set screw recess 65.

In some embodiments, the proximal set screw driver engagement feature 62 may comprise a hexagonal shape. However, it will be understood that any driver engagement feature style or shape may be utilized without departing from the spirit or scope of the present disclosure.

FIGS. 9 and 10 show the intermediate set screw 50 and the proximal set screw 60 next to each other to illustrate their relative sizes in comparison to one another. FIG. 9 shows a side view of the intermediate set screw 50 relative to the proximal set screw 60. FIG. 10 shows a bottom view of the proximal set screw 60 relative to the intermediate set screw 50, which is visible through the proximal set screw driver engagement feature 62 of the proximal set screw 60 in FIG. 10. This differential size arrangement between the intermediate set screw 50 and the proximal set screw 60 will allow a smaller or first hexagonal driver (not shown) to pass through the proximal set screw driver engagement feature 62 of the proximal set screw 60 and then engage with the intermediate set screw driver engagement feature 52 of the intermediate set screw 50 in order to rotate the intermediate set screw 50 with the first hexagonal driver placed through the proximal set screw driver engagement feature 62 of the proximal set screw 60. Once a desired first rotational position of the intermediate set screw 50 has been achieved, the first hexagonal driver may then be removed, and a larger or second hexagonal driver (not shown) may be utilized to engage with the proximal set screw driver engagement feature 62 of the proximal set screw 60 to rotate the proximal set screw 60 to a desired second rotational position. In this manner, the intermediate set screw 50 and the proximal set screw 60 can be individually adjusted to achieve separate dual compression forces across a bone joint, as will be discussed in more detail below.

FIGS. 11 and 12 show respective assemblies of the intermediate carriage 30 and proximal carriage 40 prior to insertion within the elongate device 10.

As shown in FIG. 11, the intermediate carriage 30 may be rotatably coupled to the intermediate set screw 50 by placing the bottom of the intermediate carriage 30 through the intermediate carriage spacer 81 and then inserting the intermediate carriage lower ledge 33 sideways via the intermediate set screw loading slot 54 into the intermediate set screw recess 55. This will trap the intermediate carriage lower ledge 33 between the intermediate set screw top surface 56 and the intermediate set screw retaining ledge 53 that projects into the intermediate carriage neck 35. In this manner, the intermediate carriage 30 may be translationally coupled to the intermediate set screw 50 while being free to rotate relative to the intermediate set screw 50 about is longitudinal axis.

Once the intermediate carriage 30 has been rotatably coupled to the intermediate set screw 50, the intermediate carriage 30 assembly may be inserted into the intermediate portion chamber 14 of the elongate device 10 by aligning the one or more first anti-rotation tabs or intermediate carriage anti-rotation tab 32 with the one or more first anti-rotation slots or intermediate chamber anti-rotation slot 15, threading the intermediate set screw thread 51 into the intermediate chamber thread 16, and then rotating the intermediate set screw 50 until the intermediate carriage 30 moves distally enough that the intermediate carriage hole 31 just starts to become fully visible through the proximal end of the intermediate portion window 21. In this position, the first bone fixation device 71 can be inserted through an intermediate bone (such as a talar bone 2), through the intermediate portion window 21, and into the intermediate carriage hole 31 without any compression forces being generated yet between the first bone fixation device 71 coupled to the intermediate bone and the intermediate carriage 30. Any of the bone screws or bone fixation devices disclosed herein can include any size, shape, length, thread morphology, headed/headless configuration, etc. Compression force may then be subsequently generated by rotating the intermediate set screw 50 to move it distally and urge the intermediate carriage 30 distally within the intermediate portion chamber 14 to generate a compression force, as will be discussed below in more detail.

As shown in FIG. 12, the proximal carriage 40 may likewise be rotatably coupled to the proximal set screw 60 by placing the bottom of the proximal carriage 40 through the proximal carriage spacer 82 and then inserting the proximal carriage lower ledge 45 sideways via the proximal set screw loading slot 64 into the proximal set screw recess 65. This will trap the proximal carriage lower ledge 45 between the proximal set screw top surface 66 and the proximal set screw retaining ledge 63 that projects into the proximal carriage neck 41. In this manner, the proximal carriage 40 may be translationally coupled to the proximal set screw 60 while being free to rotate relative to the proximal set screw 60 about is longitudinal axis.

Once the proximal carriage 40 has been rotatably coupled to the proximal set screw 60, the proximal carriage 40 assembly may be inserted into the proximal portion chamber 24 of the elongate device 10 by aligning the one or more second anti-rotation tabs or proximal carriage anti-rotation tab 44 with the one or more second anti-rotation slots or proximal chamber anti-rotation slot 25, threading the proximal set screw thread 61 into the proximal chamber thread 26, and then rotating the proximal set screw 60 until the proximal carriage 40 moves distally enough that the upper proximal carriage hole 42 just starts to become fully visible through the proximal end of the upper proximal portion window 22. In this position, the second bone fixation device 72 can be inserted through a proximal bone (such as a calcaneal bone 3), through the upper proximal portion window 22, and into the upper proximal carriage hole 42 without any compression forces being generated yet between the second bone fixation device 72 coupled to the proximal bone and the proximal carriage 40. Compression force may then be subsequently generated by rotating the proximal set screw 60 to move it distally and urge the proximal carriage 40 distally within the proximal portion chamber 24 to generate a compression force, as will be discussed below in more detail.

In some embodiments, a system for providing dual compression to a bone joint may include the elongate device 10, the intermediate carriage 30, and the proximal carriage 40. The distal portion 11 of the elongate device 10 may be received within a distal bone tunnel formed in a distal bone of the bone joint, the intermediate portion 12 of the elongate device 10 may be received within an intermediate bone tunnel formed in an intermediate bone of the bone joint, and the proximal portion of the elongate device 10 may be received within a proximal bone tunnel formed in a proximal bone of the bone joint. The intermediate carriage 30 may be received within the intermediate portion 12 of the elongate device 10, and the proximal carriage 40 may be received within the proximal portion 13 of the elongate device 10. The intermediate carriage 30 may be configured to couple with the intermediate bone and translate distally within the intermediate portion 12 of the elongate device 10 to provide a first compression force 7 between the intermediate bone and the distal bone of the bone joint. The proximal carriage 40 may be configured to couple with the proximal bone and translate distally within the proximal portion 13 of the elongate device 10 to provide a second compression force 8 between the proximal bone and the intermediate bone of the bone joint.

In some embodiments, the system may also include a first bone fixation device 71 configured to couple the intermediate bone to the intermediate carriage 30, and a second bone fixation device 72 configured to couple the proximal bone to the proximal carriage 40.

In some embodiments of the system, the intermediate portion 12 of the elongate device 10 may include a first window or intermediate portion window 21 configured to receive the first bone fixation device 71 therethrough, and the proximal portion 13 of the elongate device 10 may include a second window or upper proximal portion window 22 configured to receive the second bone fixation device 72 therethrough.

In some embodiments of the system, the intermediate carriage 30 may include a first passageway or intermediate carriage hole 31 configured to receive the first bone fixation device 71 therethrough to couple the intermediate bone to the intermediate carriage 30, and the proximal carriage 40 may include a second passageway or upper proximal carriage hole 42 configured to receive the second bone fixation device 72 therethrough to couple the proximal bone to the proximal carriage 40.

In some embodiments of the system, the intermediate portion 12 of the elongate device 10 may include an intermediate chamber or intermediate portion chamber 14 configured to translatably receive the intermediate carriage 30 therein, and the proximal portion 13 of the elongate device 10 may include a proximal chamber or proximal portion chamber 24 configured to translatably receive the proximal carriage 40 therein.

In some embodiments of the system, the intermediate carriage 30 may include a first anti-rotation tab or intermediate carriage anti-rotation tab 32 receivable within a first anti-rotation slot or intermediate chamber anti-rotation slot 15 formed in the intermediate portion chamber 14 to prevent the intermediate carriage 30 from rotating as the intermediate carriage 30 translates within the intermediate portion chamber 14, and the proximal carriage 40 may include a second anti-rotation tab or proximal carriage anti-rotation tab 44 receivable within a second anti-rotation slot or proximal chamber anti-rotation slot 25 formed in the proximal portion chamber 24 to prevent the proximal carriage 40 from rotating as the proximal carriage 40 translates within the proximal portion chamber 24.

In some embodiments of the system, the intermediate chamber or intermediate portion chamber 14 may include a first internal thread or intermediate chamber thread 16 configured to threadingly engage a first set screw or intermediate set screw 50 that urges the intermediate carriage 30 distally to provide the first compression force 7 between the intermediate bone and the distal bone of the bone joint, and the proximal portion chamber 24 may include a second internal thread or proximal chamber thread 26 configured to threadingly engage a second set screw or proximal set screw 60 that urges the proximal carriage 40 distally to provide the second compression force 8 between the proximal bone and the intermediate bone of the bone joint.

In some embodiments, the first compression force 7 and the second compression force 8 may be independently selected and applied to a bone joint.

In some embodiments, the first compression force 7 may be equal to the second compression force 8.

In some embodiments, the first compression force 7 may not be equal to the second compression force 8.

In some embodiments, the first compression force 7 may be less than the second compression force 8.

In some embodiments, the first compression force 7 may be greater than the second compression force 8.

In some embodiments, the first compression force 7 may increase when a second compression force 8 is subsequently applied to a bone joint.

In some embodiments, the first compression force 7 may increase by the magnitude of a second compression force when the second compression force 8 is subsequently applied to a bone joint.

In some embodiments, the first compression force 7 may increase by less than the magnitude of a second compression force when the second compression force 8 is subsequently applied to a bone joint.

In some embodiments, the intermediate portion window 21 may be shaped or elongated to provide up to or at least 1 mm of internal tibiotalar compression.

In some embodiments, the intermediate portion window 21 may be shaped or elongated to provide up to or at least 2 mm of internal tibiotalar compression.

In some embodiments, the intermediate portion window 21 may be shaped or elongated to provide up to or at least 3 mm of internal tibiotalar compression.

In some embodiments, the intermediate portion window 21 may be shaped or elongated to provide up to or at least 4 mm of internal tibiotalar compression.

In some embodiments, the intermediate portion window 21 may be shaped or elongated to provide up to or at least 5 mm of internal tibiotalar compression.

In some embodiments, the intermediate portion window 21 may be shaped or elongated to provide up to or at least 6 mm of internal tibiotalar compression.

In some embodiments, the intermediate portion window 21 may be shaped or elongated to provide up to or at least 7 mm of internal tibiotalar compression.

In some embodiments, the intermediate portion window 21 may be shaped or elongated to provide up to or at least 8 mm of internal tibiotalar compression.

In some embodiments, the intermediate portion window 21 may be shaped or elongated to provide up to or at least 9 mm of internal tibiotalar compression.

In some embodiments, the intermediate portion window 21 may be shaped or elongated to provide up to or at least 10 mm of internal tibiotalar compression.

In some embodiments, the intermediate portion window 21 may be shaped or elongated to provide more than 10 mm of internal tibiotalar compression.

In some embodiments, the upper proximal portion window 22 and/or the lower proximal portion window 23 may be shaped or elongated to provide up to or at least 1 mm of internal calcaneal-talar compression.

In some embodiments, the upper proximal portion window 22 and/or the lower proximal portion window 23 may be shaped or elongated to provide up to or at least 2 mm of internal calcaneal-talar compression.

In some embodiments, upper proximal portion window 22 and/or the lower proximal portion window 23 may be shaped or elongated to provide up to or at least 3 mm of internal calcaneal-talar compression.

In some embodiments, upper proximal portion window 22 and/or the lower proximal portion window 23 may be shaped or elongated to provide up to or at least 4 mm of internal calcaneal-talar compression.

In some embodiments, upper proximal portion window 22 and/or the lower proximal portion window 23 may be shaped or elongated to provide up to or at least 5 mm of internal calcaneal-talar compression.

In some embodiments, upper proximal portion window 22 and/or the lower proximal portion window 23 may be shaped or elongated to provide up to or at least 6 mm of internal calcaneal-talar compression.

In some embodiments, upper proximal portion window 22 and/or the lower proximal portion window 23 may be shaped or elongated to provide up to or at least 7 mm of internal calcaneal-talar compression.

In some embodiments, upper proximal portion window 22 and/or the lower proximal portion window 23 may be shaped or elongated to provide up to or at least 8 mm of internal calcaneal-talar compression.

In some embodiments, upper proximal portion window 22 and/or the lower proximal portion window 23 may be shaped or elongated to provide up to or at least 9 mm of internal calcaneal-talar compression.

In some embodiments, upper proximal portion window 22 and/or the lower proximal portion window 23 may be shaped or elongated to provide up to or at least 10 mm of internal calcaneal-talar compression.

In some embodiments, upper proximal portion window 22 and/or the lower proximal portion window 23 may be shaped or elongated to provide more than 10 mm of internal calcaneal-talar compression.

In some embodiments, a system for providing dual compression to an ankle joint may include an intramedullary nail or elongate device 10, a talar compression carriage or intermediate carriage 30, and a calcaneal compression carriage or proximal carriage 40. The intramedullary nail may include a distal portion 11 configured to be at least partially received within an intramedullary canal 4 of a tibial bone 1 of the ankle joint, an intermediate portion 12 receivable within a first or intermediate bone tunnel 5 formed through a talar bone 2 of the ankle joint, and a proximal portion 13 receivable within a second or proximal bone tunnel 6 formed through a calcaneal bone 3 of the ankle joint. The talar compression carriage may be receivable within the intermediate portion 12 of the intramedullary nail, and the calcaneal compression carriage may be receivable within the proximal portion 13 of the intramedullary nail. The talar compression carriage may be configured to couple with the talar bone 2 and translate distally within the intermediate portion 12 of the intramedullary nail to provide a first compression force 7 between the talar bone 2 and the tibial bone 1 of the ankle joint. The calcaneal compression carriage may be configured to couple with the calcaneal bone 3 and translate distally within the proximal portion 13 of the intramedullary nail to provide a second compression force 8 between the calcaneal bone 3 and the talar bone 2 of the ankle joint.

In some embodiments, the system may also include a first bone fixation device 71 configured to couple the talar bone 2 to the talar compression carriage, and a second bone fixation device 72 configured to couple the calcaneal bone 3 to the calcaneal compression carriage.

In some embodiments of the system, the intermediate portion 12 of the intramedullary nail may include a first elongated window or intermediate portion window 21 formed through the intermediate portion 12 and configured to receive the first bone fixation device 71 therethrough, and the proximal portion 13 of the intramedullary nail may include a second elongated window or upper proximal portion window 22 formed through the proximal portion 13 and configured to receive the second bone fixation device 72 therethrough.

In some embodiments of the system, the talar compression carriage may include a first hole or intermediate carriage hole 31 configured to receive the first bone fixation device 71 therein to couple the talar bone 2 to the talar compression carriage, and the calcaneal compression carriage may include a second hole or upper proximal carriage hole 42 configured to receive the second bone fixation device 72 therein to couple the calcaneal bone 3 to the calcaneal compression carriage.

In some embodiments of the system, the intermediate portion 12 of the intramedullary nail may include an intermediate chamber or intermediate portion chamber 14 configured to translatably receive the talar compression carriage therein, and the proximal portion 13 of the intramedullary nail may include a proximal chamber or proximal portion chamber 24 configured to translatably receive the calcaneal compression carriage therein.

In some embodiments of the system, the talar compression carriage may include a first anti-rotation tab or intermediate carriage anti-rotation tab 32 configured to be received within a first anti-rotation slot or intermediate chamber anti-rotation slot 15 formed in the intermediate chamber to prevent the talar compression carriage from rotating as the talar compression carriage translates within the intermediate chamber. The calcaneal compression carriage may also include a second anti-rotation tab or proximal carriage anti-rotation tab 44 configured to be received within a second anti-rotation slot or proximal chamber anti-rotation slot 25 formed in the proximal chamber to prevent the calcaneal compression carriage from rotating as the calcaneal compression carriage translates within the proximal chamber.

In some embodiments of the system, the intermediate chamber may include a first internal thread or intermediate chamber thread 16 configured to threadingly engage a first set screw or intermediate set screw 50 configured to urge the talar compression carriage distally to provide the first compression force 7 between the talar bone 2 and the tibial bone 1 of the ankle joint. The proximal chamber may also include a second internal thread or proximal chamber thread 26 configured to threadingly engage a second set screw or proximal set screw 60 configured to urge the calcaneal compression carriage distally to provide the second compression force 8 between the calcaneal bone 3 and the talar bone 2 of the ankle joint.

Figure 13:
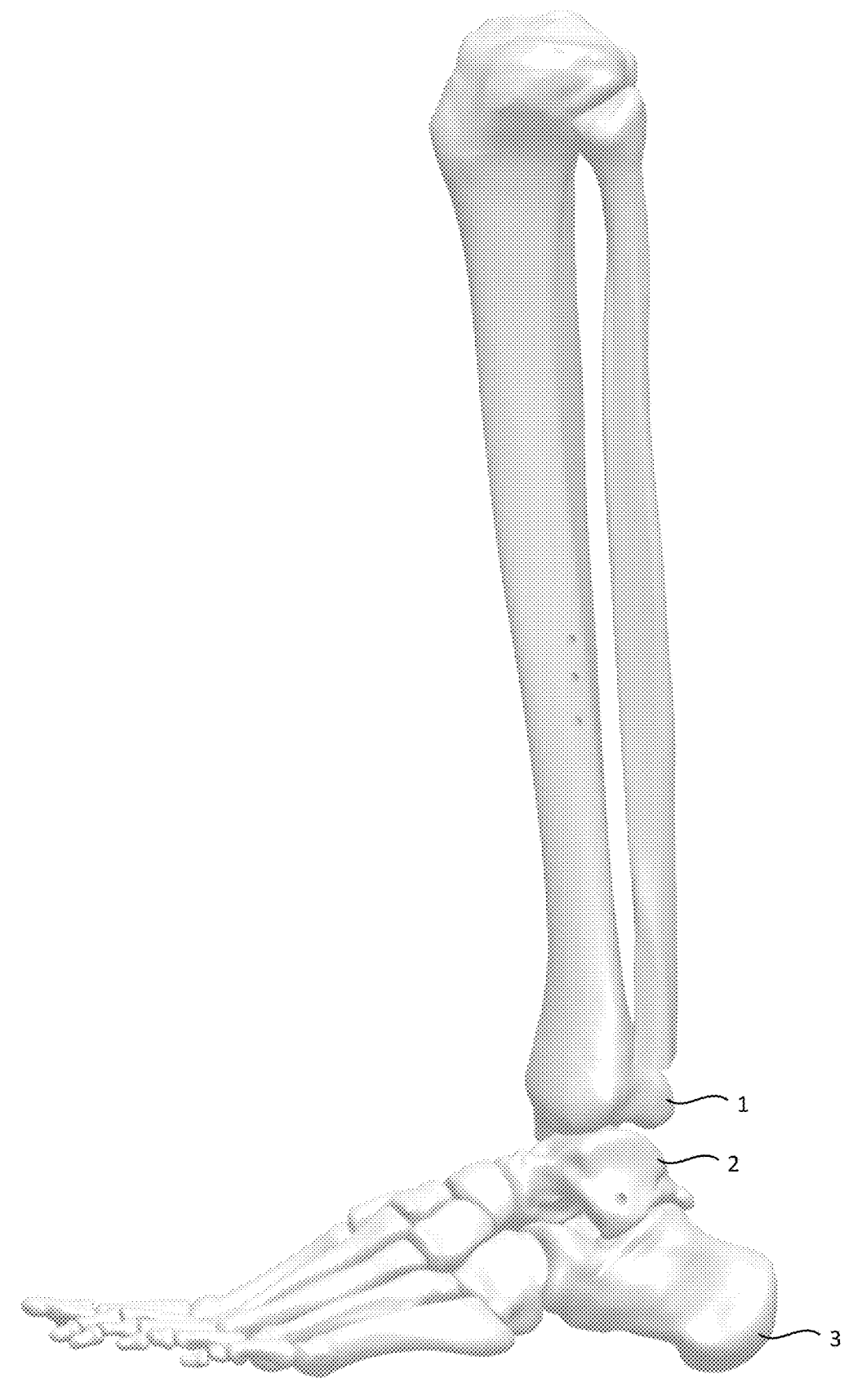
FIG. 13 illustrates a perspective side view of an ankle joint comprising a tibial bone, a talar bone, and a calcaneal bone.

FIGS. 13-21 illustrate a method for providing dual compression to a bone joint, such as the ankle joint seen in FIG. 13.

In some embodiments, the method may include holding the bone joint in a desired position (e.g., holding the hindfoot in a neutral dorsiflexion position) and preparing the bones of the bone joint (e.g., via a guide-wire assisted drilling, reaming, or broaching process, etc.) in order to form one or more bone tunnels in the bones of the joint to receive an implant. Alternatively, or in addition thereto, the implant may be pressed or otherwise forced into one or more bones of the bone joint without prepared bone tunnels.

Figure 14:
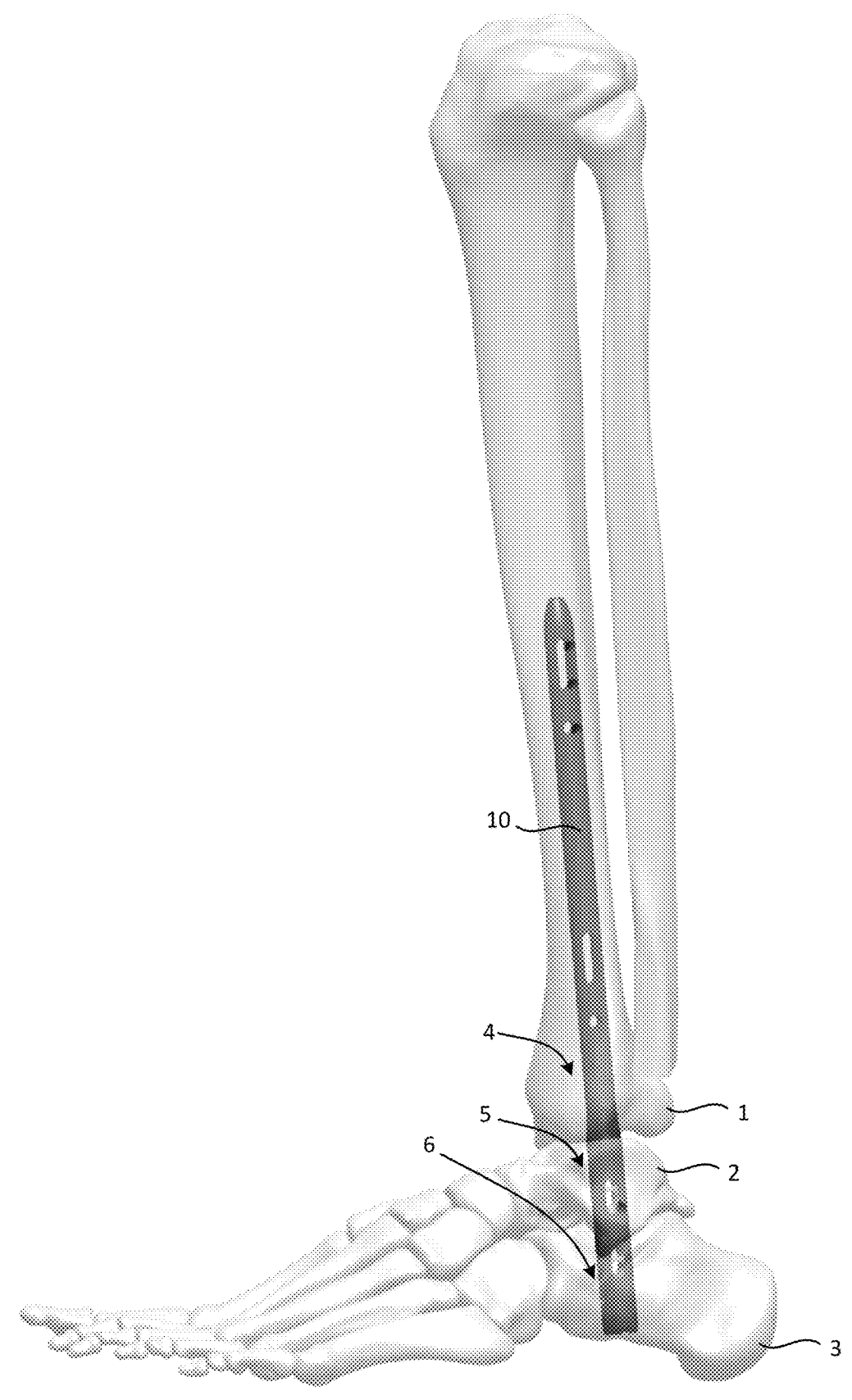
FIG. 14 illustrates a perspective side view of the elongate device from FIG. 1 inserted into the ankle joint shown in FIG. 13.

Referring to FIG. 14, in some embodiments the method may also include inserting a distal portion 11 of an elongate device 10 through a proximal bone tunnel 6 formed in a proximal bone (e.g., the calcaneal bone 3) of the bone joint, through an intermediate bone tunnel 5 formed in an intermediate bone (e.g., the talar bone 2) of the bone joint, and into a distal bone tunnel (e.g., the intramedullary canal 4) formed in a distal bone (e.g., the tibial bone 1) of the bone joint. The insertion process for the elongate device 10, as well as any subsequent bone screw or bone fixation device insertion processes described below, may be facilitated by any intramedullary nail guide instrument or targeting arm assembly (not shown) that are known or contemplated within the orthopedic technology space. In some embodiments, the distal end 18 the elongate device 10 may be counter sunk into the calcaneal bone 3 (e.g., by at least 5 mm, etc.) in order to prevent the distal end 18 of the elongate device 10 from protruding out of the calcaneal bone 3 and irritating the soft tissues on the bottom of the foot during the healing process.

Figure 15:
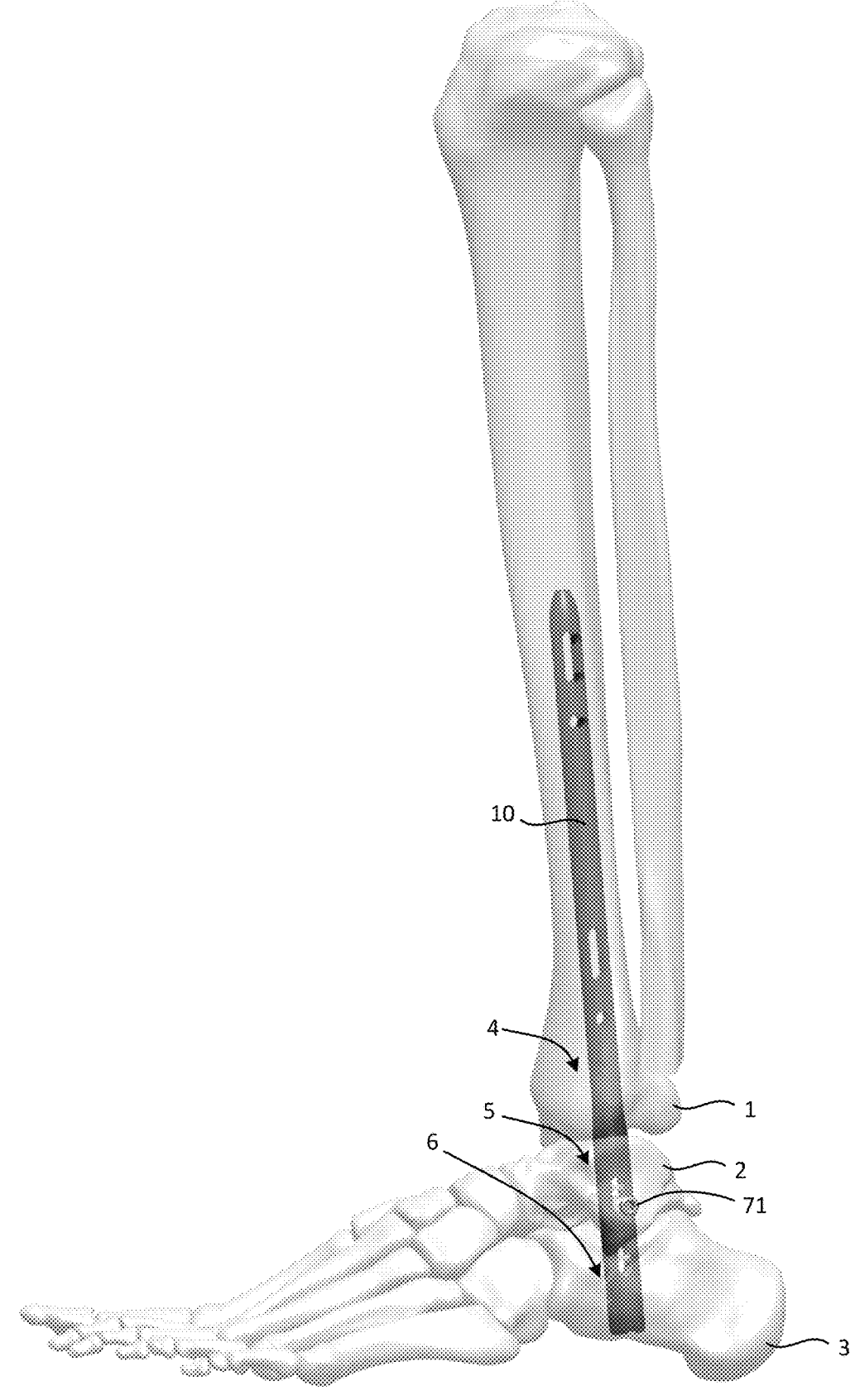
FIG. 15 illustrates a perspective side view of the ankle joint from FIG. 14 with a first bone fixation device coupling the talar bone to an intermediate carriage housed within the elongate device.

Once the elongate device 10 has been properly placed within the bones of the joint, one or more bone screws or bone fixation devices may be placed through various portions of the elongate device 10 with the aid of a nail guide instrument or targeting arm assembly (not shown), as previously discussed. For example, FIG. 15 shows the first bone fixation device 71 placed through the talar bone 2 and into the intermediate carriage hole 31 of the intermediate carriage 30 that is housed within the elongate device 10. However, it will be understood that the order of placing these bone screws or bone fixation devices through the various portions of the elongate device 10 can be performed in any order without departing from the spirit or scope of the present disclosure, and various methods with different combinations/orders for performing these steps are contemplated herein. For example, in some embodiments of the method, the first bone fixation device 71 may be placed through the elongate device 10 before the one or more distal bone fixation devices 70 are placed through the distal portion 11 of the elongate device 10, and vice-versa, etc. Thus, the following order of placing the bone screws or bone fixation devices through the elongate device 10 is for illustration purposes only and is merely one non-limiting example for performing the method steps disclosed herein. Moreover, it will also be understood that the order of compressing the bones together may be performed in any order relative to each other and/or relative to the placement of any bone screw or bone fixation device of the system without departing from the spirit or scope of the present disclosure. Thus, various methods with different combinations/orders for performing the steps of compressing the bone joint are also contemplated herein.

Continuing with FIG. 15, in some embodiments the method may also include coupling the intermediate bone (e.g., the talar bone 2) to the intermediate carriage 30 that is housed within the intermediate portion 12 of the elongate device 10. In some embodiments of the method, coupling the intermediate bone to the intermediate carriage 30 may also include inserting the first bone fixation device 71 through the intermediate bone, through a first window or the intermediate portion window 21 that is formed in the intermediate portion, and into a first passageway or the intermediate carriage hole 31 that is formed in the intermediate carriage 30 to couple the intermediate bone to the intermediate carriage 30. While the bone screws or bone fixation devices shown in the figures as being placed through the elongate device 10 from a lateral to medial direction, it will also be understood that any of the bone screws or bone fixation devices shown or contemplated herein may also be placed through the elongate device 10 from a medial to lateral direction.

Figure 16:
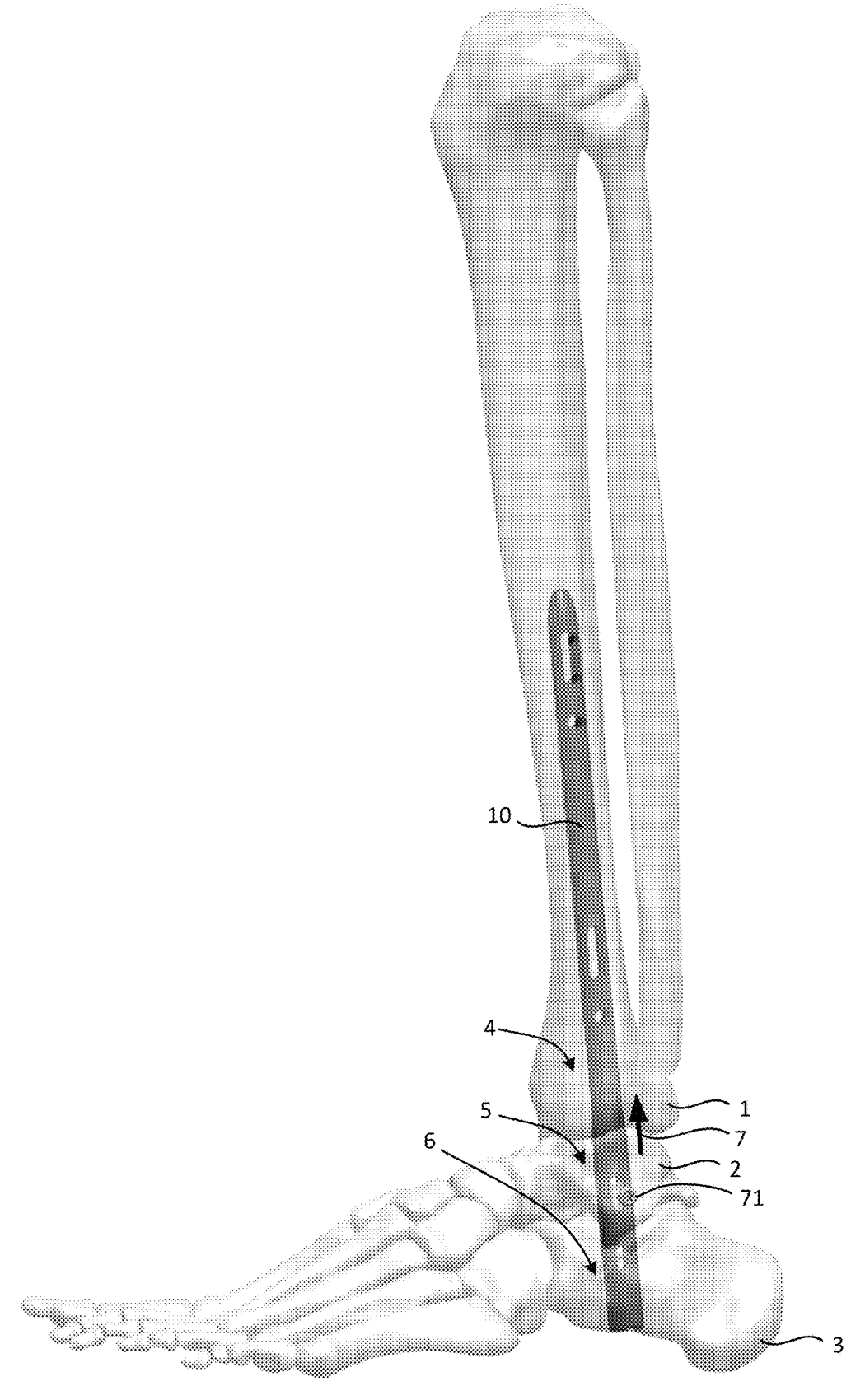
FIG. 16 illustrates a perspective side view of the ankle joint from FIG. 15 with the intermediate carriage translated distally to provide a first compression force between the talar bone and the tibial bone.

As shown in FIG. 16, in some embodiments the method may also include translating the intermediate carriage 30 distally within the intermediate portion 12 of the elongate device 10 to provide a first compression force 7 between the intermediate bone (e.g., the talar bone 2) and the distal bone (e.g., the tibial bone 1) of the bone joint. In some embodiments of the method, translating the intermediate carriage 30 distally within the intermediate portion 12 may also include rotating a first set screw or intermediate set screw 50 to urge the intermediate carriage 30 distally and provide the first compression force 7 between the intermediate bone and the distal bone of the bone joint. This may be accomplished with a smaller or first hexagonal driver (not shown), as previously discussed. Moreover, a torque limiting mechanism or torque limiting driver (not shown) may also be utilized to achieve a first desired torque level corresponding to the first compression force 7, and/or to prevent overtightening of the intermediate set screw 50.

Figure 17:
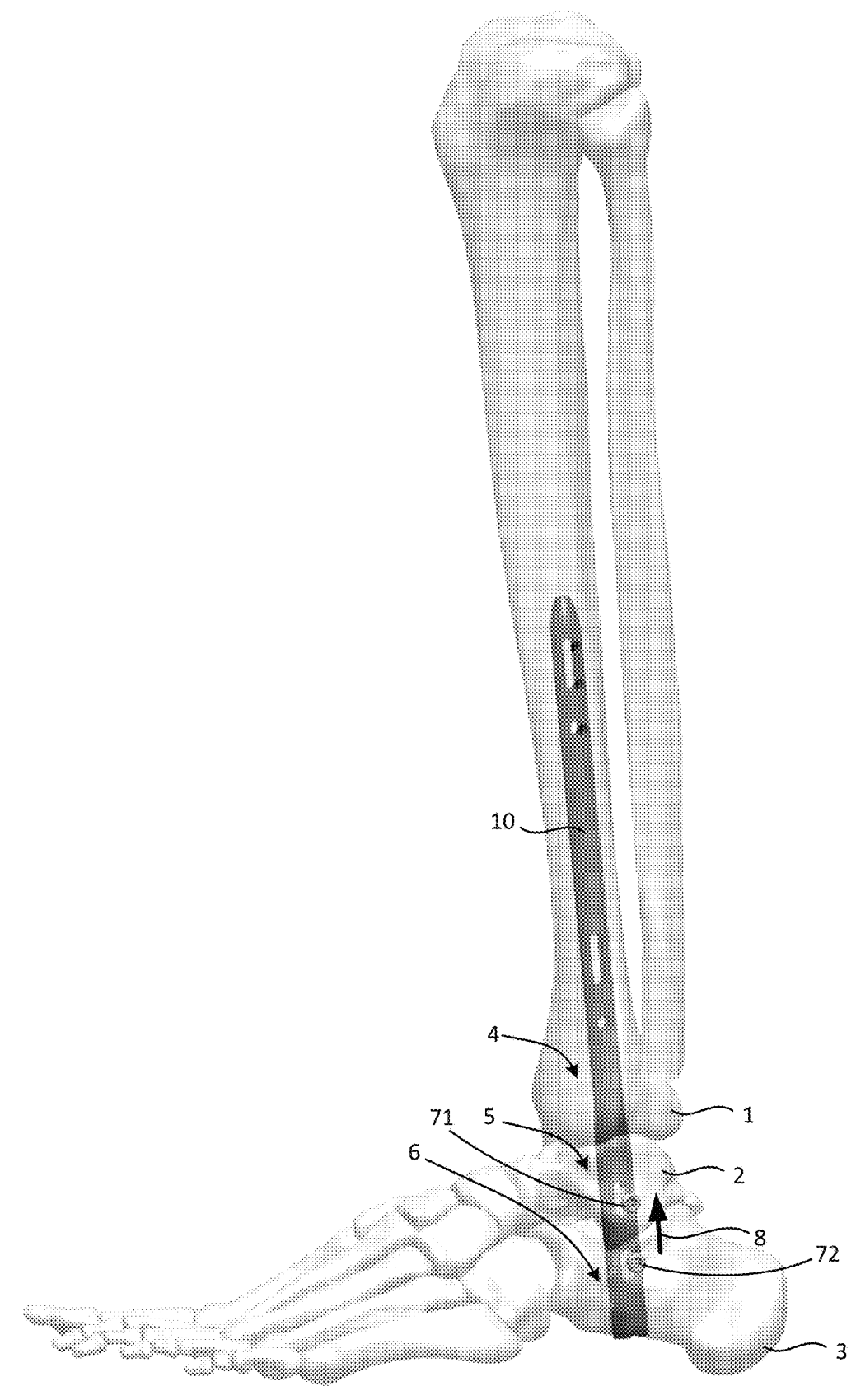
FIG. 17 illustrates a perspective side view of the ankle joint from FIG. 16 with a second bone fixation device coupling the calcaneal bone to a proximal carriage housed within the elongate device that is translated distally to provide a second compression force between the calcaneal bone and the talar bone.

As shown in FIG. 17, in some embodiments the method may also include coupling the proximal bone (e.g., the calcaneal bone 3) to the proximal carriage 40 that is housed within the proximal portion 13 of the elongate device 10. In some embodiments of the method, coupling the proximal bone to the proximal carriage 40 may also include inserting the second bone fixation device 72 through the proximal bone, through a second window or the upper proximal portion window 22 that is formed in the proximal portion 13 of the elongate device 10, and into a second passageway or the upper proximal carriage hole 42 that is formed in the proximal carriage 40 to couple the proximal bone to the proximal carriage 40.

Continuing with FIG. 17, in some embodiments the method may also include translating the proximal carriage 40 distally within the proximal portion 13 of the elongate device 10 to provide the second compression force 8 between the proximal bone (e.g., the calcaneal bone 3) and the intermediate bone (e.g., the talar bone 2) of the bone joint. In some embodiments of the method, translating the proximal carriage 40 distally within the proximal portion 13 may also include rotating a second set screw or the proximal set screw 60 to urge the proximal carriage 40 distally and provide the second compression force 8 between the proximal bone and the intermediate bone of the bone joint. This may be accomplished with a larger or second hexagonal driver (not shown), as previously discussed. Moreover, a torque limiting mechanism or torque limiting driver (not shown) may likewise be utilized to achieve a second desired torque level corresponding to the second compression force 8, and/or to prevent overtightening of the proximal set screw 60.

Figure 18:
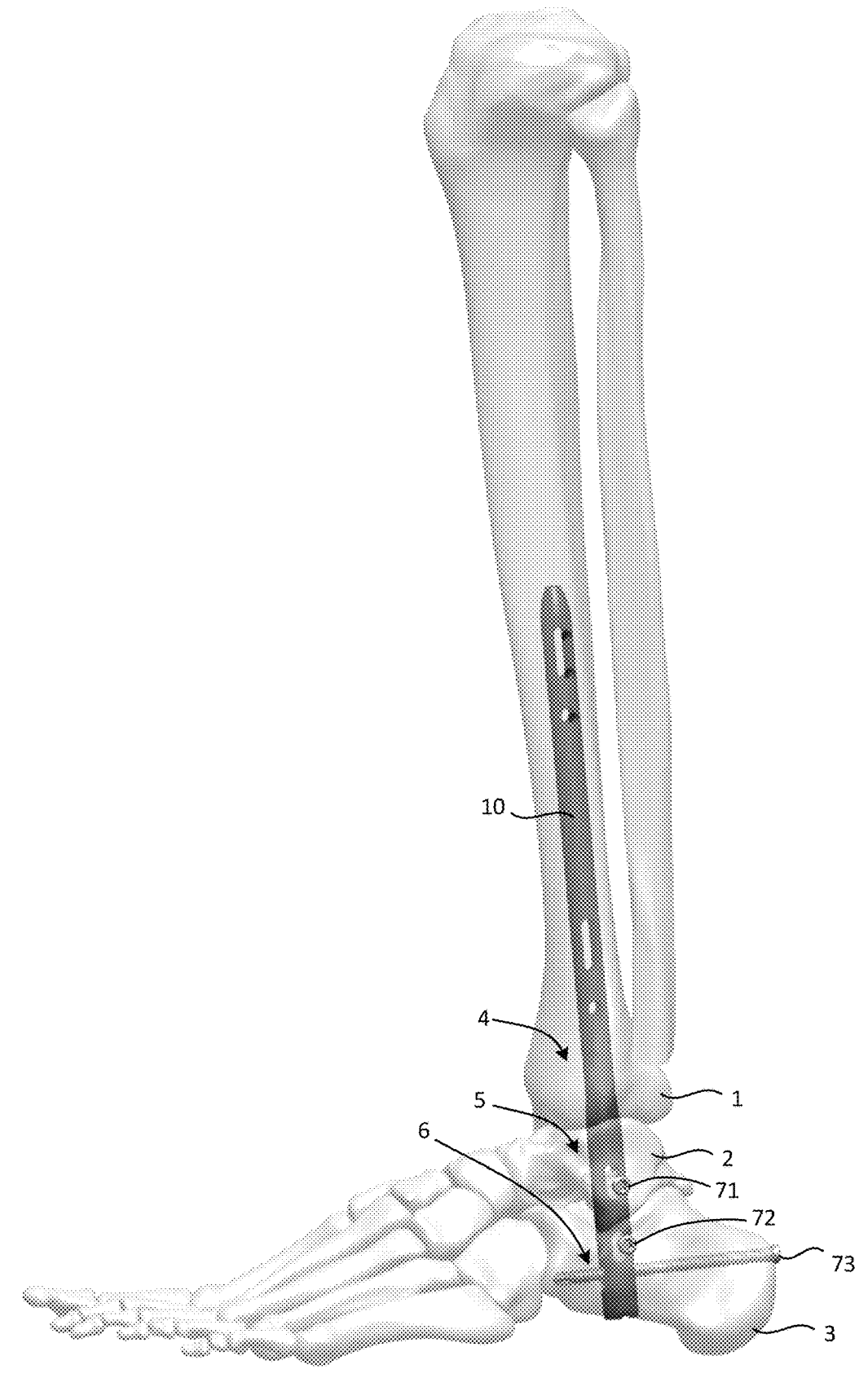
FIG. 18 illustrates a perspective side view of the ankle joint from FIG. 17 with a third bone fixation device coupling the calcaneal bone to the proximal carriage.

As shown in FIG. 18, in some embodiments the method may also include inserting a third bone fixation device 73 through the proximal bone, through a third window or lower proximal portion window 23 that is formed in the proximal portion 13 of the elongate device 10, and into a third passageway or lower proximal carriage hole 43 that is formed in the proximal carriage 40 to further couple the proximal bone to the proximal carriage 40 in a second place and provide additional stability/strength.

Figure 19:
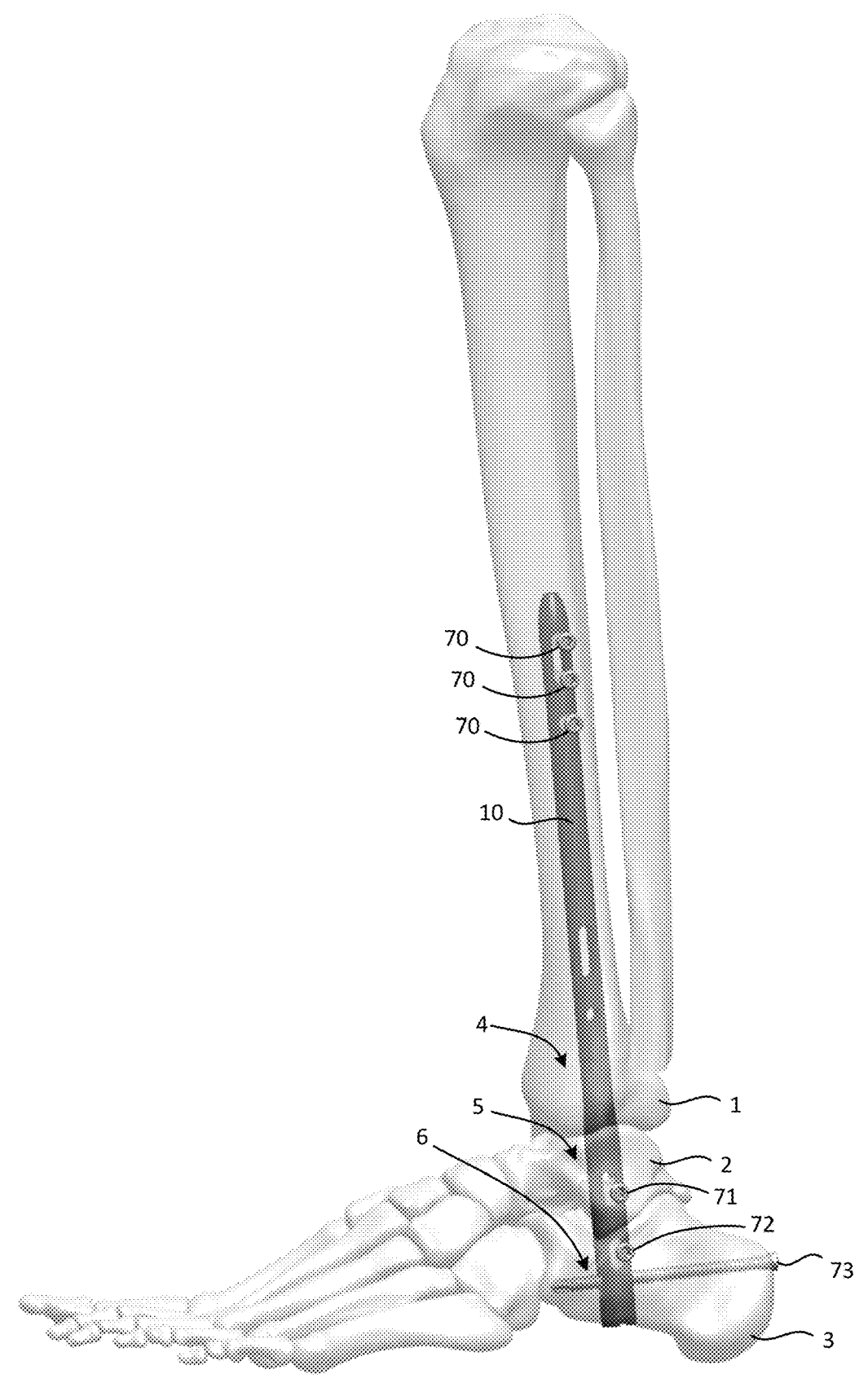
FIG. 19 illustrates a perspective side view of the ankle joint from FIG. 18 with distal bone fixation devices coupling the elongate device to the tibia.

As shown in FIG. 19, in some embodiments the method may also include inserting one or more distal bone fixation devices 70 through the distal bone (e.g., the tibial bone 1) to further stabilize the elongate device 10 relative to the distal bone. As previously discussed, the one or more distal bone fixation devices 70 may be inserted prior any other bone screw and/or prior to any of the compression steps.

Figure 20:
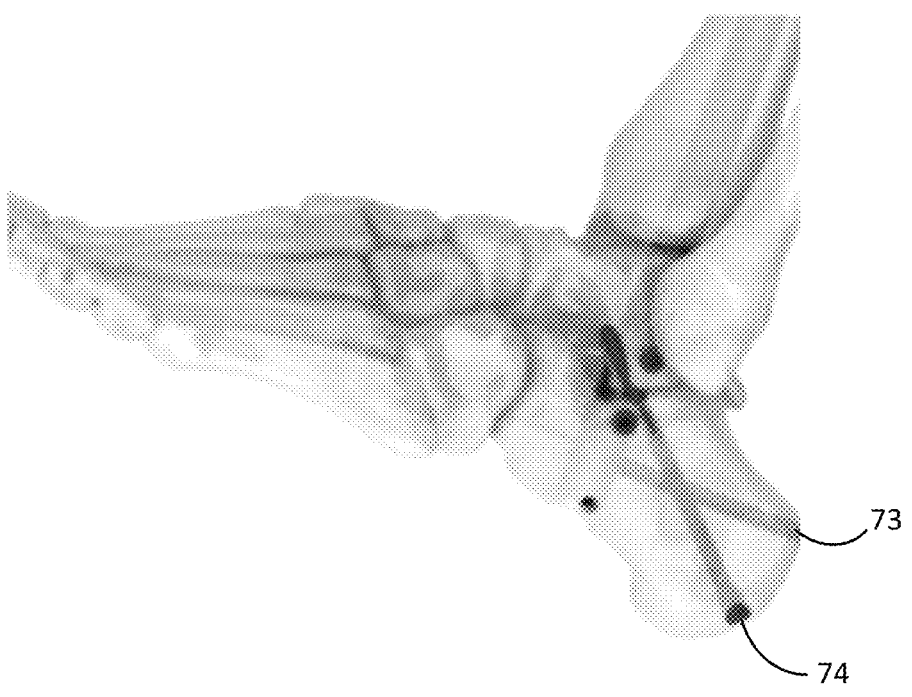
FIG. 20 illustrates a perspective side view of the ankle joint from FIG. 19 with a fourth oblique bone fixation device coupling the calcaneal bone to the talar bone.
Figure 21:
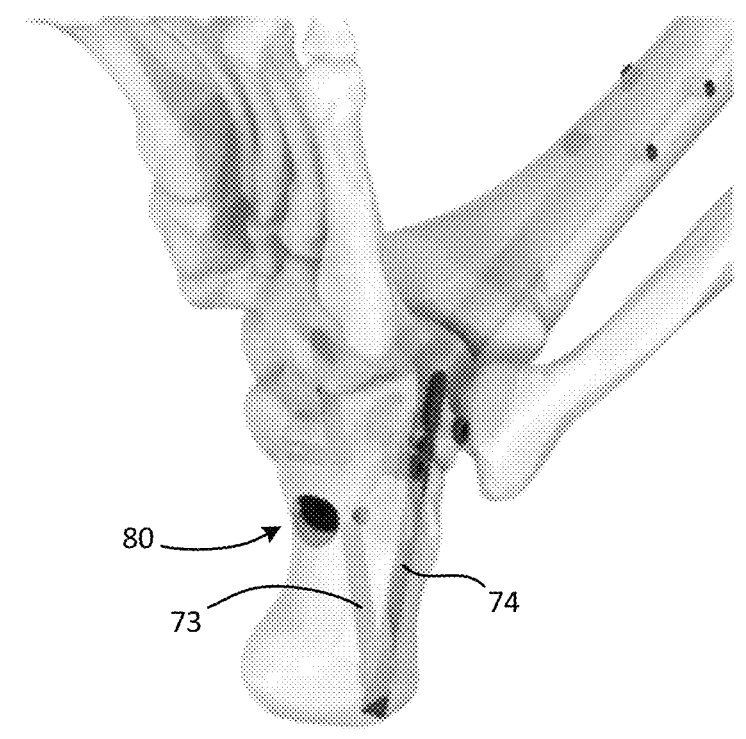
FIG. 21 illustrates a perspective bottom view of the ankle joint from FIG. 20 with a cap installed on the distal end of the elongate device.

As shown in FIG. 20, in some embodiments the method may also include inserting an oblique bone fixation device or a fourth bone fixation device 74 through the proximal bone (e.g., the calcaneal bone 3) and into the intermediate bone (e.g., the talar bone 2) to provide additional fixation, stability, compression maintenance, etc., between the proximal bone and the intermediate bone. The angle of the fourth bone fixation device 74 relative to the can first bone fixation device 71 can be any angle (e.g., 22.5 degrees, 45 degrees, etc.). Moreover, the fourth bone fixation device 74 may be placed laterally or medially relative to the elongate device 10.

As shown in FIG. 20, in some embodiments the method may also include placing a cap 80 on the distal end 18 of the elongate device 10 to cover any sharp edges of the distal end 18 of the elongate device 10 and also prevent soft tissue in-growth into the proximal portion chamber 24 to facilitate a revision surgery in the future, as needed. Moreover, different cap sizes with different internal lengths (not shown) may also be utilized to internally abut up against the proximal end 67 of the proximal set screw 60 to prevent the proximal set screw 60 from backing out over time. If a revision surgery is needed, removal of the implant system can be performed in essentially the reverse order of the installation procedures that are described herein.

Any procedures or methods disclosed herein comprise one or more steps or actions for performing the described procedure or method. The method steps and/or actions may be interchanged with one another. In other words, unless a specific order of steps or actions is required for proper operation of the embodiment, the order and/or use of specific steps and/or actions may be modified. Moreover, any of the methods or procedures described herein may be further modified by omitting, deleting, and/or adding any of the method, procedure steps, or actions described or contemplated herein.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, drawing, or description thereof for the purpose of streamlining the present disclosure. This method of disclosure, however, is not to be interpreted as reflecting an intention that any embodiment or claim require more features than those expressly recited in that embodiment or claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112. It will be apparent to those having skill in the art that changes may be made to the details of the above-described embodiments without departing from the underlying principles set forth herein.

The phrases "connected to", "coupled to", and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−10% of a target value, measurement, or desired characteristic.

It will be understood than any feature or group of features described or contemplated herein with respect to any implant, system, method, or instrument may be combined in any fashion with any other implant, system, method, or instrument that is described or contemplated herein in order to make any number of different implant, system, method, or instrument configurations.

While specific embodiments and applications of the present disclosure have been illustrated and described, it is to be understood that the scope of this disclosure or the appended claims are not limited to the precise configuration and components disclosed herein. Various modifications, changes, and variations which will be apparent to those skilled in the art may be made in the arrangement, operation, and details of the devices, implants, systems, methods, or instruments disclosed herein.

What is claimed is:

1. A system for providing dual compression to an ankle joint comprising:
    an intramedullary nail comprising:
        a distal portion configured to be at least partially received within an intramedullary canal of a tibial bone of the ankle joint;
        an intermediate portion receivable within a first bone tunnel formed through a talar bone of the ankle joint; and
        a proximal portion receivable within a second bone tunnel formed through a calcaneal bone of the ankle joint;
    a talar compression carriage receivable within the intermediate portion of the intramedullary nail; and
    a calcaneal compression carriage receivable within the proximal portion of the intramedullary nail,
    wherein:
        the talar compression carriage is configured so that, with the talar compression carriage received in the intermediate portion and the calcaneal compression carriage received in the proximal portion, the talar compression carriage is independently moveable along a longitudinal axis of the intermediate portion relative to the calcaneal compression carriage;
        the talar compression carriage is configured to couple with the talar bone and translate distally within the intermediate portion of the intramedullary nail to provide a first compression force between the talar bone and the tibial bone of the ankle joint; and
        the calcaneal compression carriage is configured to couple with the calcaneal bone and translate distally within the proximal portion of the intramedullary nail to provide a second compression force between the calcaneal bone and the talar bone of the ankle joint.

2. The system of claim 1, further comprising:
    a first bone fixation device configured to couple the talar bone to the talar compression carriage; and
    a second bone fixation device configured to couple the calcaneal bone to the calcaneal compression carriage.

3. The system of claim 2, wherein:
    the intermediate portion of the intramedullary nail comprises a first elongated window formed through the intermediate portion and configured to receive the first bone fixation device therethrough; and
    the proximal portion of the intramedullary nail comprises a second elongated window formed through the proximal portion and configured to receive the second bone fixation device therethrough.

4. The system of claim 2, wherein:
    the talar compression carriage comprises a first hole configured to receive the first bone fixation device therein to couple the talar bone to the talar compression carriage; and
    the calcaneal compression carriage comprises a second hole configured to receive the second bone fixation device therein to couple the calcaneal bone to the calcaneal compression carriage.

5. The system of claim 1, wherein:
    the intermediate portion of the intramedullary nail comprises an intermediate chamber configured to translatably receive the talar compression carriage therein; and
    the proximal portion of the intramedullary nail comprises a proximal chamber configured to translatably receive the calcaneal compression carriage therein.

6. The system of claim 5, wherein:
    the talar compression carriage comprises a first anti-rotation tab configured to be received within a first anti-rotation slot formed in the intermediate chamber to prevent the talar compression carriage from rotating as the talar compression carriage translates within the intermediate chamber; and
    the calcaneal compression carriage comprises a second anti-rotation tab configured to be received within a second anti-rotation slot formed in the proximal chamber to prevent the calcaneal compression carriage from rotating as the calcaneal compression carriage translates within the proximal chamber.

7. The system of claim 5, wherein:
    the intermediate chamber comprises a first internal thread configured to threadingly engage a first set screw that is configured to urge the talar compression carriage distally to provide the first compression force between the talar bone and the tibial bone of the ankle joint; and
    the proximal chamber comprises a second internal thread configured to threadingly engage a second set screw that is configured to urge the calcaneal compression carriage distally to provide the second compression force between the calcaneal bone and the talar bone of the ankle joint.

8. A system for providing dual compression to a bone joint comprising:
    an elongate device comprising:
        a distal portion receivable within a distal bone tunnel formed in a distal bone of the bone joint;
        an intermediate portion receivable within an intermediate bone tunnel formed in an intermediate bone of the bone joint; and
        a proximal portion receivable within a proximal bone tunnel formed in a proximal bone of the bone joint;
    an intermediate carriage receivable within the intermediate portion of the elongate device; and
    a proximal carriage receivable within the proximal portion of the elongate device,
    wherein:
        the intermediate carriage is configured so that, with the intermediate carriage received in the intermediate portion, the intermediate carriage is coaxial with the intermediate portion;
        the proximal carriage is configured so that, with the proximal carriage received in the proximal portion, the proximal carriage is coaxial with the proximal portion;
        the intermediate carriage is configured to couple with the intermediate bone and translate distally within the intermediate portion of the elongate device to provide a first compression force between the intermediate bone and the distal bone of the bone joint; and
        the proximal carriage is configured to couple with the proximal bone and translate distally within the proximal portion of the elongate device to provide a second compression force between the proximal bone and the intermediate bone of the bone joint.

9. The system of claim 8, further comprising:
a first bone fixation device configured to couple the intermediate bone to the intermediate carriage; and
a second bone fixation device configured to couple the proximal bone to the proximal carriage.

10. The system of claim 9, wherein:
the intermediate portion of the elongate device comprises a first window configured to receive the first bone fixation device therethrough; and
the proximal portion of the elongate device comprises a second window configured to receive the second bone fixation device therethrough.

11. The system of claim 9, wherein:
the intermediate carriage comprises a first passageway configured to receive the first bone fixation device therethrough to couple the intermediate bone to the intermediate carriage; and
the proximal carriage comprises a second passageway configured to receive the second bone fixation device therethrough to couple the proximal bone to the proximal carriage.

12. The system of claim 8, wherein:
the intermediate portion of the elongate device comprises an intermediate chamber configured to translatably receive the intermediate carriage therein; and
the proximal portion of the elongate device comprises a proximal chamber configured to translatably receive the proximal carriage therein.

13. The system of claim 12, wherein:
the intermediate carriage comprises a first anti-rotation tab configured to be received within a first anti-rotation slot formed in the intermediate chamber to prevent the intermediate carriage from rotating as the intermediate carriage translates within the intermediate chamber; and
the proximal carriage comprises a second anti-rotation tab configured to be received within a second anti-rotation slot formed in the proximal chamber to prevent the proximal carriage from rotating as the proximal carriage translates within the proximal chamber.

14. The system of claim 12, wherein:
the intermediate chamber comprises a first internal thread configured to threadingly engage a first set screw that is configured to urge the intermediate carriage distally to provide the first compression force between the intermediate bone and the distal bone of the bone joint; and
the proximal chamber comprises a second internal thread configured to threadingly engage a second set screw that is configured to urge the proximal carriage distally to provide the second compression force between the proximal bone and the intermediate bone of the bone joint.

15. A system for providing dual compression to an ankle joint comprising:
an intramedullary nail comprising:
a distal portion configured to be at least partially received within an intramedullary canal of a tibial bone of the ankle joint;
an intermediate portion receivable within a first bone tunnel formed through a talar bone of the ankle joint; and
a proximal portion receivable within a second bone tunnel formed through a calcaneal bone of the ankle joint;
a talar compression carriage receivable within the intermediate portion of the intramedullary nail; and a calcaneal compression carriage receivable within the proximal portion of the intramedullary nail,
wherein:
the talar compression carriage is configured to be received in an intermediate set screw through an intermediate circumferential spacer;
the calcaneal compression carriage is configured to be received in a proximal set screw through a proximal circumferential spacer;
the talar compression carriage is configured to couple with the talar bone and translate distally within the intermediate portion of the intramedullary nail to provide a first compression force between the talar bone and the tibial bone of the ankle joint; and
the calcaneal compression carriage is configured to couple with the calcaneal bone and translate distally within the proximal portion of the intramedullary nail to provide a second compression force between the calcaneal bone and the talar bone of the ankle joint.

16. The system of claim 15, further comprising:
a first bone fixation device configured to couple the talar bone to the talar compression carriage; and
a second bone fixation device configured to couple the calcaneal bone to the calcaneal compression carriage.

17. The system of claim 16, wherein:
the intermediate portion of the intramedullary nail comprises a first elongated window formed through the intermediate portion and configured to receive the first bone fixation device therethrough; and
the proximal portion of the intramedullary nail comprises a second elongated window formed through the proximal portion and configured to receive the second bone fixation device therethrough.

18. The system of claim 15, wherein:
the intermediate portion of the intramedullary nail comprises an intermediate chamber configured to translatably receive the talar compression carriage therein; and
the proximal portion of the intramedullary nail comprises a proximal chamber configured to translatably receive the calcaneal compression carriage therein.

19. The system of claim 18, wherein:
the talar compression carriage comprises a first anti-rotation tab configured to be received within a first anti-rotation slot formed in the intermediate chamber to prevent the talar compression carriage from rotating as the talar compression carriage translates within the intermediate chamber; and
the calcaneal compression carriage comprises a second anti-rotation tab configured to be received within a second anti-rotation slot formed in the proximal chamber to prevent the calcaneal compression carriage from rotating as the calcaneal compression carriage translates within the proximal chamber.

20. The system of claim 18, wherein:
the intermediate chamber comprises a first internal thread configured to threadingly engage the intermediate set screw that is configured to urge the talar compression carriage distally to provide the first compression force between the talar bone and the tibial bone of the ankle joint; and
the proximal chamber comprises a second internal thread configured to threadingly engage the proximal set screw that is configured to urge the calcaneal compression carriage distally to provide the second compres-
sion force between the calcaneal bone and the talar
bone of the ankle joint.

* * * * *